(12) United States Patent
Logan et al.

(10) Patent No.: US 10,828,168 B2
(45) Date of Patent: Nov. 10, 2020

(54) PATIENT SPECIFIC COMPOSITE KNEE REPLACEMENT

(71) Applicant: Howmedica Osteonics Corp., Mahwah, NJ (US)

(72) Inventors: Scott G. Logan, Oak Ridge, NJ (US); Aaron Essner, Bloomingdale, NJ (US)

(73) Assignee: Howmedica Osteonics Corp., Mahwah, NJ (US)

( * ) Notice: Subject to any disclaimer, the term of this patent is extended or adjusted under 35 U.S.C. 154(b) by 75 days.

(21) Appl. No.: 15/971,540

(22) Filed: May 4, 2018

(65) Prior Publication Data

US 2018/0325683 A1 Nov. 15, 2018

Related U.S. Application Data

(60) Provisional application No. 62/504,067, filed on May 10, 2017.

(51) Int. Cl.
*A61F 2/38* (2006.01)
*A61F 2/30* (2006.01)

(52) U.S. Cl.
CPC .............. *A61F 2/3859* (2013.01); *A61F 2/38* (2013.01); *A61F 2/389* (2013.01); *A61F 2/3868* (2013.01); *A61F 2/3872* (2013.01); *A61F 2/3877* (2013.01); *A61F 2002/30014* (2013.01); *A61F 2002/3863* (2013.01)

(58) Field of Classification Search
CPC combination set(s) only.
See application file for complete search history.

(56) References Cited

U.S. PATENT DOCUMENTS

| | | |
|---|---|---|
| 3,715,763 A | 2/1973 | Link |
| 4,055,862 A | 11/1977 | Farling |
| 4,344,193 A | 8/1982 | Kenny |
| 4,502,161 A | 3/1985 | Wall |
| 4,728,332 A | 3/1988 | Albrektsson |
| 4,919,667 A | 4/1990 | Richmond |
| 5,007,934 A | 4/1991 | Stone |
| 5,067,964 A | 11/1991 | Richmond et al. |
| 5,171,322 A | 12/1992 | Kenny |
| 5,308,412 A | 5/1994 | Shetty et al. |
| 5,683,469 A | 11/1997 | Johnson et al. |
| 5,735,903 A | 4/1998 | Li et al. |

(Continued)

*Primary Examiner* — Yashita Sharma
(74) *Attorney, Agent, or Firm* — Lerner, David, Littenberg, Krumholz & Mentlik, LLP

(57) ABSTRACT

A prosthetic knee implant system includes a prosthetic femoral component and a prosthetic tibial component. The femoral component includes a lateral condyle, a medial condyle, a bone-contacting surface that may be formed of porous metal, and an articular surface that may be formed of PAEK/PEEK. The tibial component includes medial and lateral condylar portions, a bone-contacting surface that may be formed of porous metal, and a second surface opposite the bone-contacting surface. Recesses extend a depth into the second surfaces of the medial and lateral condylar portions. Medial and lateral bearing inserts with flat proximal faces are positioned with the recesses of the medial and lateral condylar portions. Flexible medial and lateral meniscal components are positioned to surround the medial and lateral inserts, respectively, and extend proximal to the second surface of the insert.

19 Claims, 20 Drawing Sheets

(56) References Cited

U.S. PATENT DOCUMENTS

| | | |
|---|---|---|
| 5,879,387 A | 3/1999 | Jones et al. |
| 6,042,610 A | 3/2000 | Li et al. |
| 6,059,831 A | 5/2000 | Braslow et al. |
| 6,206,927 B1 | 3/2001 | Fell et al. |
| 6,344,059 B1 | 2/2002 | Krakovits et al. |
| 6,503,280 B2 | 1/2003 | Repicci |
| 6,629,997 B2 | 10/2003 | Mansmann |
| 6,679,914 B1 | 1/2004 | Gabbay |
| 6,916,341 B2 | 7/2005 | Rolston |
| 6,923,831 B2 | 8/2005 | Fell et al. |
| 6,994,730 B2 | 2/2006 | Posner |
| 7,066,963 B2 | 6/2006 | Naegerl |
| 7,163,563 B2 | 1/2007 | Schwartz et al. |
| 7,261,740 B2 | 8/2007 | Tuttle et al. |
| 7,291,169 B2 | 11/2007 | Hodorek |
| 7,320,709 B2 | 1/2008 | Felt et al. |
| 7,341,602 B2 | 3/2008 | Fell et al. |
| 7,611,653 B1 | 11/2009 | Elsner et al. |
| 7,625,407 B2 | 12/2009 | Akizuki et al. |
| 7,670,381 B2 | 3/2010 | Schwartz |
| 7,799,077 B2 | 9/2010 | Lang et al. |
| 7,799,087 B2 | 9/2010 | Howald et al. |
| 7,806,896 B1 | 10/2010 | Bonutti |
| 7,806,897 B1 | 10/2010 | Bonutti |
| 7,828,852 B2 | 11/2010 | Bonutti |
| 7,828,853 B2 | 11/2010 | Ek et al. |
| 7,837,736 B2 | 11/2010 | Bonutti |
| 7,892,236 B1 | 2/2011 | Bonutti |
| 7,931,690 B1 | 4/2011 | Bonutti |
| 7,959,635 B1 | 6/2011 | Bonutti |
| 7,976,578 B2 | 7/2011 | Marvel |
| 7,991,599 B2 | 8/2011 | Linder-Ganz et al. |
| 7,998,205 B2 | 8/2011 | Hagen et al. |
| 8,016,884 B2 | 9/2011 | Shterling et al. |
| 8,029,574 B2 | 10/2011 | Kellar et al. |
| 8,080,059 B2 | 12/2011 | Fell |
| 8,128,703 B2 | 3/2012 | Hazebrouck et al. |
| 8,142,510 B2 | 3/2012 | Lee et al. |
| 8,147,558 B2 | 4/2012 | Lee et al. |
| 8,162,961 B2 | 4/2012 | Zaporojan et al. |
| 8,173,162 B2 | 5/2012 | Vilei et al. |
| 8,192,491 B2 | 6/2012 | Fox |
| 8,287,594 B2 | 10/2012 | Cragg et al. |
| 8,287,601 B2 | 10/2012 | Wagner et al. |
| 8,308,807 B2 | 11/2012 | Seebeck et al. |
| 8,317,870 B2 | 11/2012 | Wagner et al. |
| 8,328,874 B2 | 12/2012 | Lee |
| 8,343,227 B2 | 1/2013 | Metzger et al. |
| 8,361,147 B2 | 1/2013 | Shterling et al. |
| 8,394,149 B2 | 3/2013 | Howald et al. |
| 8,425,522 B2 | 4/2013 | Bonutti |
| 8,506,637 B2 | 8/2013 | Schwartz |
| 8,512,413 B2 | 8/2013 | Kellar et al. |
| 8,545,569 B2 | 10/2013 | Fitz et al. |
| 8,597,362 B2 | 12/2013 | Shenoy et al. |
| 8,608,759 B2 | 12/2013 | Zaporojan et al. |
| 8,608,801 B2 | 12/2013 | Hung et al. |
| 8,623,030 B2 | 1/2014 | Bonutti |
| 8,632,552 B2 | 1/2014 | Bonutti |
| 8,632,601 B2 | 1/2014 | Howald et al. |
| 8,641,726 B2 | 2/2014 | Bonutti |
| 8,657,881 B2 | 2/2014 | Kladakis et al. |
| 8,668,739 B2 | 3/2014 | Blanchard et al. |
| 8,690,955 B2 | 4/2014 | Rolston |
| 8,702,802 B2 | 4/2014 | Linares et al. |
| 8,753,401 B2 | 6/2014 | Dee |
| 8,753,403 B2 | 6/2014 | Linares et al. |
| 8,784,495 B2 | 7/2014 | Bonutti |
| 8,828,080 B2 | 9/2014 | Fell |
| 8,834,490 B2 | 9/2014 | Bonutti |
| 8,840,629 B2 | 9/2014 | Bonutti |
| 8,845,724 B2 | 9/2014 | Shenoy et al. |
| 8,845,746 B2 | 9/2014 | Wagner et al. |
| 8,852,284 B2 | 10/2014 | Wiley et al. |
| 8,858,557 B2 | 10/2014 | Bonutti |
| 8,864,835 B2 | 10/2014 | Linares et al. |
| 8,911,502 B2 | 12/2014 | Li et al. |
| 8,920,498 B2 | 12/2014 | Buma et al. |
| 8,968,403 B2 | 3/2015 | Luginbuhl et al. |
| 8,968,404 B2 | 3/2015 | Dee |
| 8,979,935 B2 | 3/2015 | Lozier et al. |
| 8,999,000 B2 | 4/2015 | Hodorek et al. |
| 9,011,547 B2 | 4/2015 | Auger et al. |
| 9,060,797 B2 | 6/2015 | Bonutti |
| 9,101,443 B2 | 8/2015 | Bonutti |
| 9,114,016 B2 | 8/2015 | Shenoy et al. |
| 9,155,625 B2 | 10/2015 | Dee |
| 9,192,459 B2 | 11/2015 | Bonutti |
| 9,204,967 B2 | 12/2015 | Wyss et al. |
| 9,278,004 B2 | 3/2016 | Shenoy et al. |
| 9,283,077 B2 | 3/2016 | Amis et al. |
| 9,320,606 B2 | 4/2016 | Fox |
| 9,326,863 B2 | 5/2016 | Linder-Ganz et al. |
| 9,381,089 B2 | 7/2016 | Linder-Ganz et al. |
| 9,398,956 B2 | 7/2016 | Hazebrouck et al. |
| 9,427,334 B2 | 8/2016 | Axelson, Jr. et al. |
| 9,468,466 B1 | 10/2016 | Shenoy et al. |
| 2001/0023373 A1 | 9/2001 | Plouhar et al. |
| 2002/0022884 A1 | 2/2002 | Mansmann |
| 2002/0022889 A1 | 2/2002 | Chibrac et al. |
| 2002/0147498 A1 | 10/2002 | Tallarida et al. |
| 2002/0173855 A1 | 11/2002 | Mansmann |
| 2003/0055501 A1 | 3/2003 | Fell et al. |
| 2003/0060888 A1 | 3/2003 | Fell et al. |
| 2005/0033424 A1 | 2/2005 | Fell |
| 2005/0177238 A1 | 8/2005 | Khandkar et al. |
| 2008/0133008 A1 | 6/2008 | Truncale et al. |
| 2008/0243262 A1 | 10/2008 | Lee |
| 2008/0243263 A1 | 10/2008 | Lee et al. |
| 2012/0239159 A1* | 9/2012 | Metzger ............... A61F 2/3836 623/20.28 |
| 2013/0030528 A1 | 1/2013 | Chen et al. |
| 2013/0085569 A1 | 4/2013 | Hedman et al. |
| 2013/0173008 A1 | 7/2013 | Bechtold et al. |
| 2013/0304209 A1 | 11/2013 | Schmieding et al. |
| 2013/0312897 A1 | 11/2013 | Vowles |
| 2013/0317619 A1 | 11/2013 | Goodfellow et al. |
| 2013/0325137 A1* | 12/2013 | Trimmer ............... A61F 2/3868 623/20.33 |
| 2014/0031933 A1 | 1/2014 | Gatt et al. |
| 2014/0180420 A1 | 6/2014 | Gatt et al. |
| 2014/0222149 A1 | 8/2014 | Amis et al. |
| 2014/0256229 A1 | 9/2014 | Zhang et al. |
| 2014/0277451 A1 | 9/2014 | Ganz et al. |
| 2014/0277530 A1 | 9/2014 | Stalcup et al. |
| 2015/0190234 A1 | 7/2015 | Wei et al. |
| 2015/0305873 A1 | 10/2015 | Sanford et al. |
| 2016/0151162 A1 | 6/2016 | Wyss et al. |
| 2016/0206435 A1 | 7/2016 | Nocco et al. |
| 2016/0228256 A1 | 8/2016 | Fox |
| 2018/0296349 A1* | 10/2018 | Stalcup ............... B29C 66/727 |

\* cited by examiner

PATIENT SPECIFIC COMPOSITE KNEE REPLACEMENT

CROSS-REFERENCE TO RELATED APPLICATIONS

The present application claims the benefit of the filing date of U.S. Provisional Patent Application No. 62/504,067, filed May 10, 2017, the disclosure of which is hereby incorporated by reference herein.

BACKGROUND OF THE DISCLOSURE

This disclosure relates to surgical implants that are designed to replace meniscal tissue and cartilage in a mammalian joint, such as a knee joint, and methods to implant the same.

Compared to other joints such as the hip, the knee has a greater dependence on passive soft tissues (e.g. menisci, cartilage, and ligaments) for stability and function. Knee implants often consist of rigid on semi-rigid bearing surfaces, such as cobalt chrome ("CoCr") on polyethylene. In many prosthetic knee implants, function and mobility are impaired because rigid structures are used to replace the natural soft tissues.

Normal anatomical knees have two pliable, mobile menisci—a medial meniscus and a lateral meniscus—that function to absorb shock, distribute stress, increase joint congruity, increase contact area, guide arthrokinematics, help lubrication by maintaining a fluid-film bearing surface, and provide proprioceptive input, e.g., nerve impulse via meniscal attachment to the joint capsule. Even under physiologic loading a natural knee with natural menisci will primarily distribute stresses through a fluid film, only 10% of a load is transmitted via a solid on solid contact. Due to the fluid film bearing surface contact wear is greatly reduced. In simple terms the menisci function to reduce joint stresses, decrease wear, and help guide normal kinematics. Without menisci, peak contact stresses in the knee increase by 235% or more and degenerative changes start to progress rapidly. At 0°, 30°, and 60° of flexion, natural knees with intact menisci have approximately 6 to 8 times the contact area of typical prosthetic knee implants many of which have a similar geometry to that of a natural knee without menisci.

Typical prosthetic knee replacements attempt to recreate natural kinematics of the knee by using substantially flat tibial bearing components to articulate with respect to a prosthetic femoral component, or using "deep dish" tibial bearing components to articulate with respect to a prosthetic femoral component. Flat tibial bearing components may be suitable to replicate cartilage surfaces, but when used alone may suffer shortcomings. For example, flat tibial bearings may be subject to paradoxical posterior-to-anterior sliding of the femur with respect to the tibia with associated instability of the joint and limited range of motion at extreme flexion. Deep dish inserts, on the other hand, attempt to replicate the function of the menisci at the extremes of joint range of motion. This level of rigid constraint may increase the propensity for edge loading and may perform poorly at the outer bounds of the range of motion of the joint (e.g. deep flexion or extension).

Although significant progress has been made in prosthetic knee joint designs, prosthetic knees that replicate function of the healthy knee through the entire range of motion remain elusive.

BRIEF SUMMARY

According to a first aspect of the disclosure, a prosthetic knee implant system includes a prosthetic femoral component and a prosthetic tibial component. The femoral component includes a lateral condyle, a medial condyle, a bone-contacting surface, and an articular surface, the bone-contacting surface being formed at least partially of porous metal and the articular surface formed at least partially of a polyaryl ether ketone ("PAEK"). The tibial component includes a base, lateral and medial bearing inserts, and lateral and medial meniscal components. The base has a bone-contacting surface, a second surface opposite the bone-contacting surface, a lateral condylar portion and a medial condylar portion. The bearing inserts are at least partially formed of polyethylene. The meniscal components are at least partially formed of polyurethane. In an assembled condition of the tibial component, the lateral insert fits within a recess of the lateral condylar portion, the medial insert fits within a recess of the medial condylar portion, the lateral meniscal component is engaged with an extends proximally from the lateral condylar portion, and the medial meniscal component is engaged with and extends proximally from the medial condylar portion.

The base may include a bridge coupling the lateral condylar portion to the medial condylar portion so that an anterior notch is formed between the medial and lateral condylar portions anterior to the bridge, and a posterior notch is formed between the medial and lateral condylar portions posterior to the bridge. The base may include a medial protrusion extending distally from the bone-contacting surface of the medial condylar portion and a lateral protrusion extending distally from the lateral condylar portion. The medial and lateral protrusions may each be substantially "D"-shaped. The medial protrusion and lateral protrusion may each include a distal surface formed of porous metal. The second surface may be formed of polished metal. The second surface may be coated with PAEK. The medial meniscal component may extend around a circumference of the medial insert and the lateral meniscal component may extend around a circumference of the lateral insert in the assembled condition of the tibial component. The medial meniscal component may include a side wall and a peripheral rim extending radially outward of the side wall, and the lateral meniscal component may include a side wall and a peripheral rim extending radially outward of the side wall, and in the assembled condition of the tibial component the second surface of the base may overlie the peripheral rims of the medial and lateral meniscal components. The bone-contacting surface of the femoral component may include a main contact surface and a peripheral rim extending along a perimeter of the main contact surface of the femoral component, the peripheral rim of the femoral component extending substantially orthogonally away from the main contact surface of the femoral component.

According to another aspect of the disclosure, a prosthetic knee implant system includes a prosthetic femoral component and a prosthetic tibial component. The femoral component has a lateral condyle, a medial condyle, a bone-contacting surface, and an articular surface. The tibial component has a base, lateral and medial bearing inserts, and flexible lateral and medial meniscal components. The base has a lateral condylar portion having a lateral recess formed therein and a medial condylar portion having a medial recess formed therein, the base having a bone-contacting surface and a second surface opposite the bone-contacting surface, the medial and lateral recesses extending a depth into the second surface. The lateral bearing insert is secured within the lateral recess in an assembled condition of the tibial component, the lateral bearing insert having a flat proximal surface for articulation with the lateral condyle of the femoral component. The medial bearing insert is secured within the medial recess in the assembled condition of the tibial component, the medial bearing insert having a flat proximal surface for articulation with the medial condyle of the femoral component. The flexible lateral meniscal component is positioned at least partially within the lateral recess and has a main contact surface extending around a circumference of the lateral insert and extending proximally of the second surface for supporting the lateral condyle of the femoral component in the assembled condition of the tibial component. The flexible medial meniscal component is positioned at least partially within the medial recess and has a main contact surface extending around a circumference of the medial insert and extending proximally of the second surface for supporting the medial condyle of the femoral component in the assembled condition of the tibial component The base includes a bridge coupling the lateral condylar portion to the medial condylar portion so that an anterior notch is formed between the medial and lateral condylar portions anterior to the bridge, and a posterior notch is formed between the medial and lateral condylar portions posterior to the bridge.

The base may include a medial protrusion extending distally from the bone-contacting surface of the medial condylar portion and a lateral protrusion extending distally from the lateral condylar portion. The medial and lateral protrusions may each be substantially "D"-shaped. The medial protrusion and lateral protrusion may each include a distal surface formed of porous metal. The bone-contacting surfaces of the femoral component and the tibial component may each be at least partially formed of porous metal, the medial and lateral inserts may each be at least partially formed of polyethylene, the articular surface of the femoral component may be at least partially formed of a polyaryl ether ketone ("PAEK"), and the medial and lateral meniscal components may each be at least partially formed of polyurethane. The second surface may be formed of polished metal. The second surface may be coated with PAEK. The medial meniscal component may include a side wall and a peripheral rim extending radially outward of the side wall, and the lateral meniscal component may include a side wall and a peripheral rim extending radially outward of the side wall, and in the assembled condition of the tibial component the second surface of the base may overlie the peripheral rims of the medial and lateral meniscal components. The bone-contacting surface of the femoral component may include a main contact surface and a peripheral rim extending along a perimeter of the main contact surface of the femoral component, the peripheral rim of the femoral component extending substantially orthogonally away from the main contact surface of the femoral component. The main contact surfaces of the medial and lateral meniscal components may be wedge-shaped such that portions of the medial and lateral components nearer the bridge extend a greater height proximal to the second surface than portions of the medial and lateral components positioned farther away from the bridge in the assembled condition of the tibial component.

DETAILED DESCRIPTION

As used herein, the term "distal" means more distant from the heart and the term "proximal" means closest to the heart. The term "inferior" means toward the feet and the term "superior" means towards the head. The term "anterior" means towards the front part of the body or the face and the term "posterior" means towards the back of the body. The term "medial" means toward the midline of the body and the term "lateral" means away from the midline of the body. As used herein, the terms "generally," "substantially," and "about" are intended to mean the slight deviations from absolute are included within the scope of the term so modified. Like numbers refer to similar or identical elements throughout.

A healthy knee joint includes the interface between the distal end of the femur and the proximal end of the tibia. If the healthy knee joint becomes damaged due, for example, to injury or disease, knee surgery may be required to restore normal structure and function of the joint. If the damage to the knee is severe, total knee arthroplasty ("TKA") may be required. TKA typically involves the removal of the damaged portion of joint and the replacement of the damaged portion of the joint with one or more prosthetic components.

To avoid interference with surrounding native tissues, prosthetic components may need to be configured or adapted to closely match the anatomy of the bone to avoid excessive overhang and/or impingement of the implant into the surrounding soft tissues of the joint. For example, in some TKA procedures, one or more of cruciate ligaments (e.g. the anterior cruciate ligament ("ACL") and/or posterior cruciate ligament ("PCL")) may be left intact, to be re-used with the prosthetic implants to form the new knee joint. In these "cruciate retaining" applications, the prosthetic implant components may be configured to avoid interference with or impingement on the retained cruciate ligament(s) in the intercondylar area of the knee joint.

Figure 1:
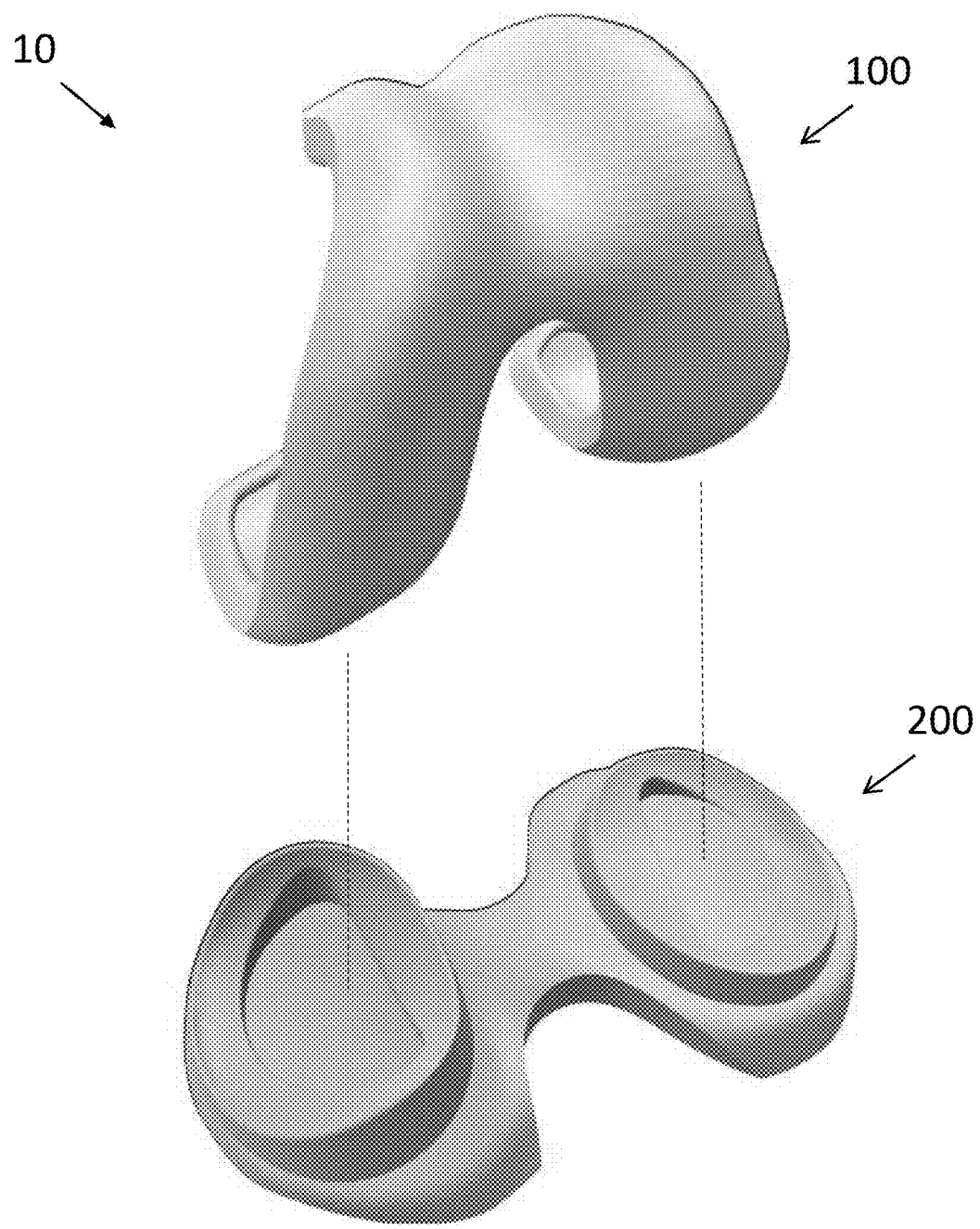
FIG. 1 is a perspective view of a femoral component and tibial component of a prosthetic implant system.

FIG. 1 illustrates a perspective view of a prosthetic knee implant system 10. In the embodiment illustrated in FIG. 1, prosthetic implant system 10 may include a plurality of components, each of which is configured to replace a respective resected portion of a native knee joint. In this embodiment, prosthetic implant system 10 includes a femoral implant component 100 configured to replace a resected portion of a native femur, and a tibial implant component 200 configured to replace a resected portion of a native tibia. After installation during knee replacement surgery, femoral component 100 and tibial component 200 cooperate to replicate the form and function of a native knee joint, although in some situations the femoral implant system may be used without the tibial implant system and vice versa.

Referring now to FIGS. 2A-E, femoral implant component 100 is adapted to be secured to the distal end of femur 300 and to replace the structure and function of the native femoral portion of the knee joint by any suitable method, including those described in greater detail below. Femoral component 100 may include a medial condyle 110 and a lateral condyle 120 configured to replace resected medial and lateral condyles of the native femur 300, and to articulate with respect to corresponding medial and lateral condylar portions of tibial component 200. The medial condyle 110 and lateral condyle 120 may be separated by an intercondylar notch 140, which may provide a channel through which one or more of the cruciate ligaments may pass.

Femoral component 100 may also include a patellar guide portion 150. When implanted on the native femur 300, the patellar guide portion 150 may extend from the anterior of the distal portion of the femur and curve distally and posteriorly toward the intercondylar fossa of the femur, which is exposed by intercondylar notch 140. The medial condyle 110 and lateral condyle 120 project from the bottom of patellar guide portion 150 and extend on either side of intercondylar notch 140 around the distalmost end of the femur 300 and continue toward the posterior femur. Patellar guide portion 150 may be configured to emulate the structure and function of the native patellar surface, which is located on the anterior of the distal portion of femur 300. For example, patellar guide portion 150 may include a groove 152 that is located toward the center of patellar guide portion. Located on either side of groove 152 and directly above medial condyle 110 and lateral condyle 120 is a raised surface 154, 156, respectively. Groove 152 provides the surface that articulates with the patella (or "kneecap," not shown), while raised surfaces 154, 156 help prevent the patella from sliding outside of groove 152.

Figure 2A:
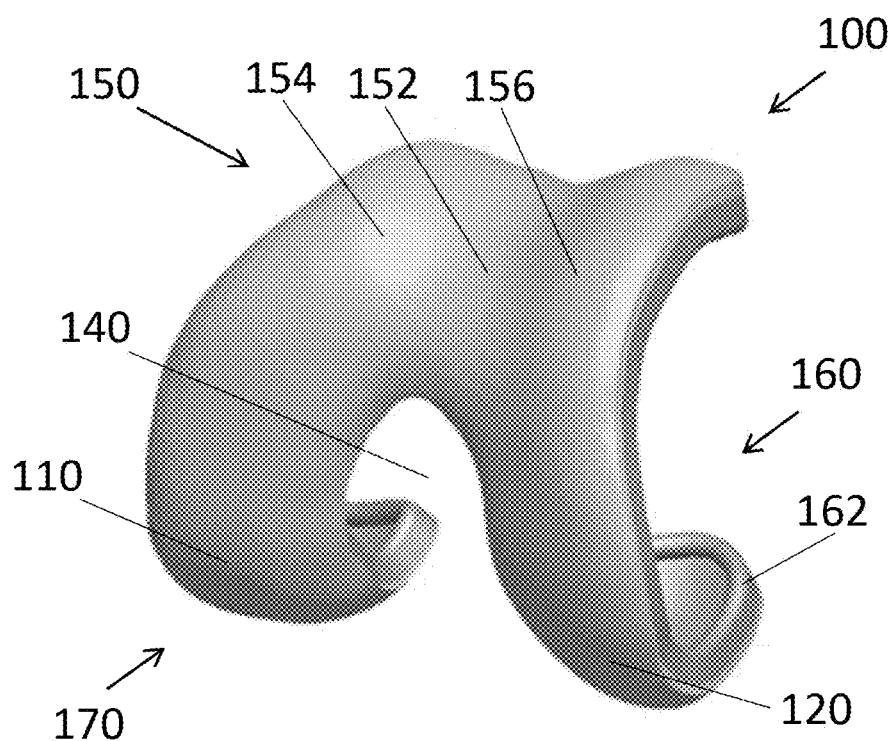
FIGS. 2A-E are various views of the femoral component of FIG. 1.
Figure 2B:
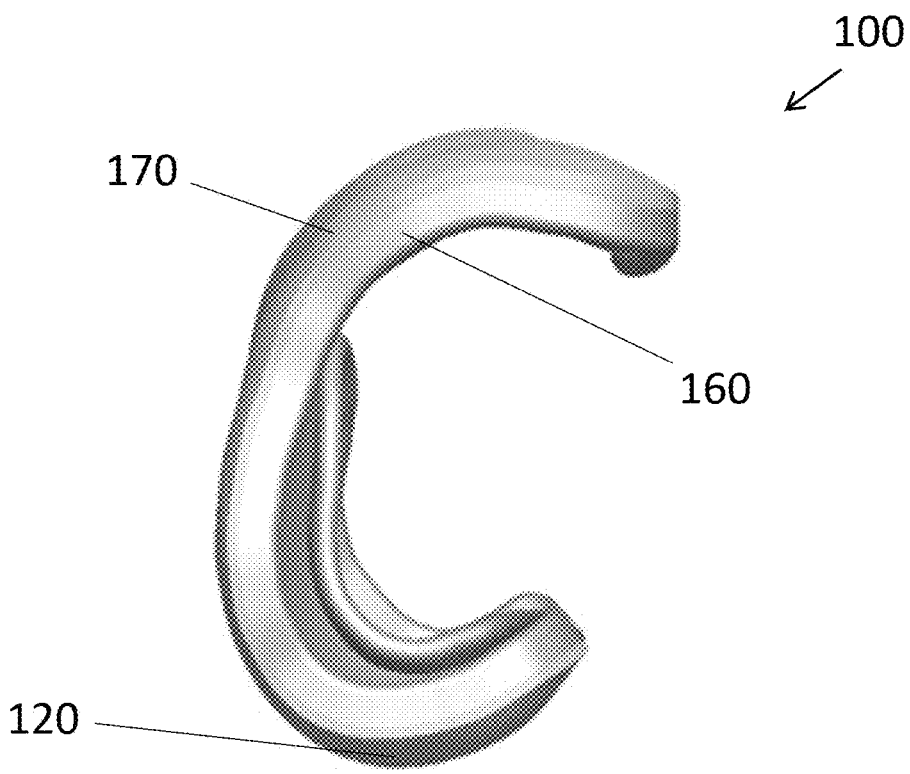
Figure 2C:
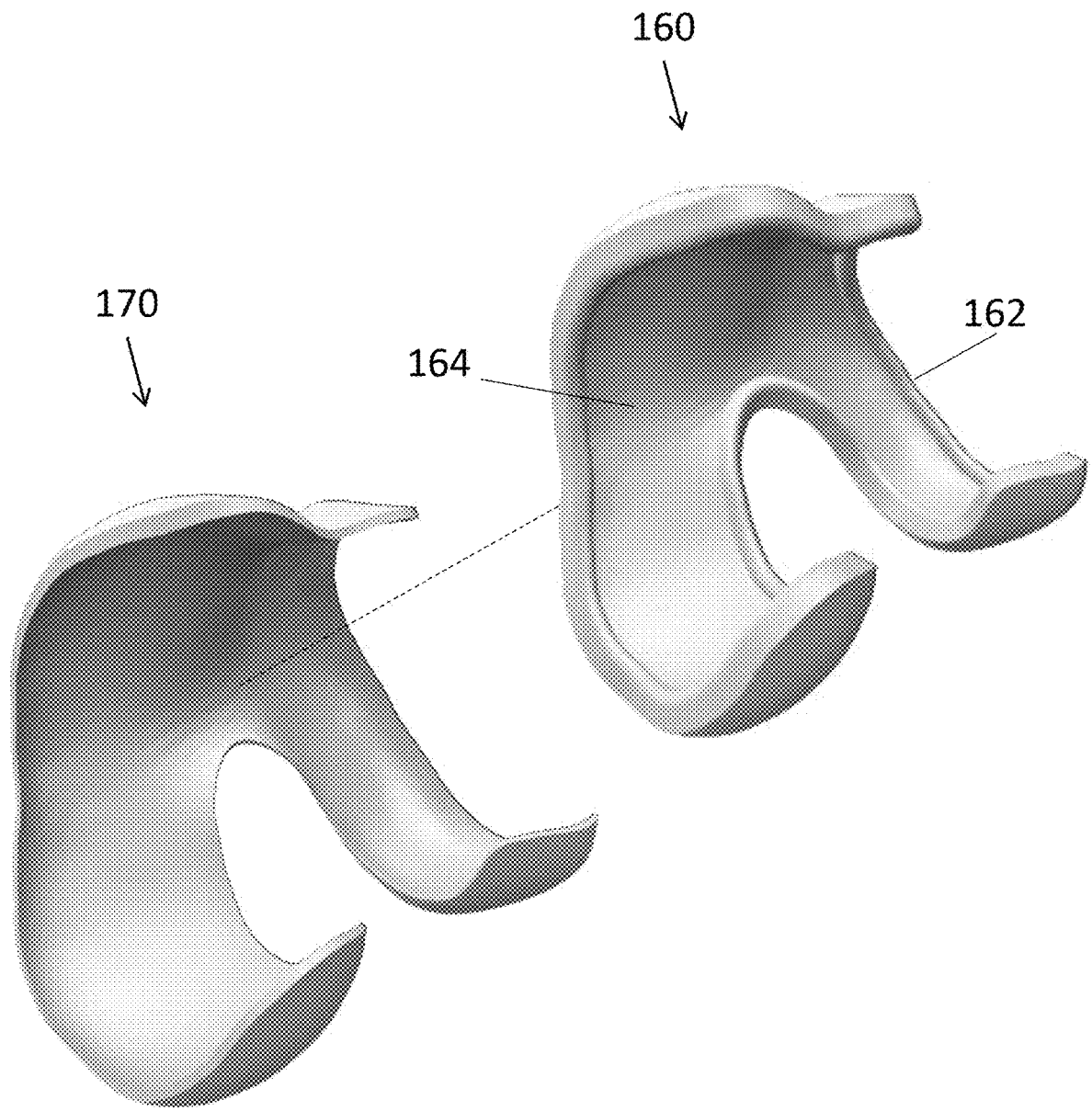
Figure 2D:
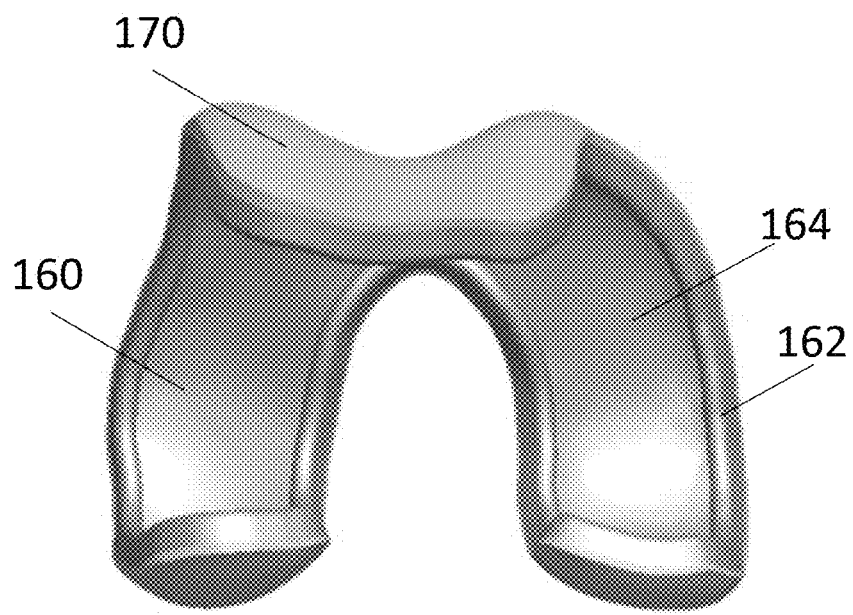
Figure 2E:
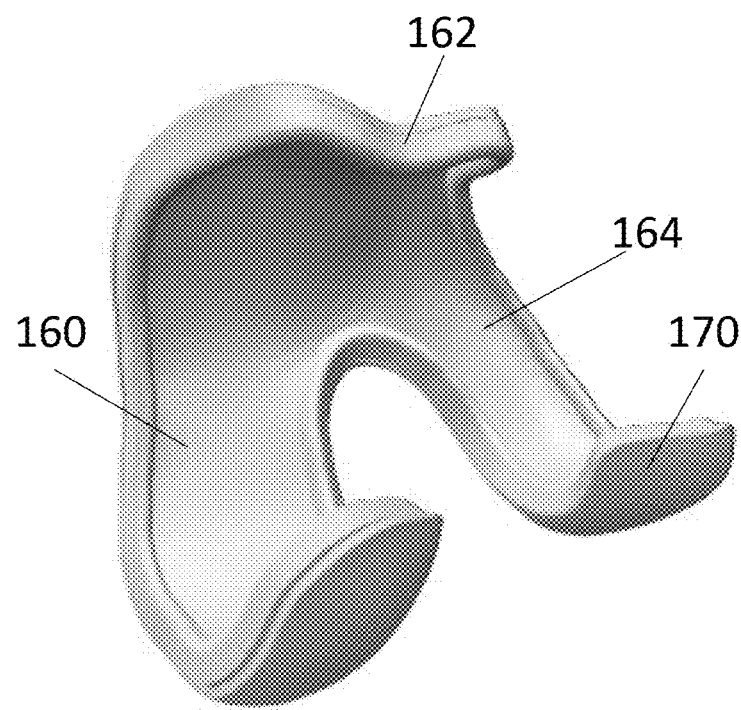

Femoral component 100 may include an interior bone-contacting surface 160 and an exterior articular surface 170. Bone-contacting surface 160 is configured to engage with the resected surface(s) of femur 300. In the illustrated embodiment, bone-contacting surface 160 is curved and intended to contact a correspondingly curved portion of the resected femur 300. Methods to resect femur 300 with such curvature may be achieved with robotic surgical tools. However, in other embodiments, bone-contacting surface 160 may include a plurality of planar surfaces, each of which may correspond to a resected plane of the femur that has been prepared using a planar cutting tool. Bone-contacting surface 160 may be formed with a peripheral rim 162 extending along part or all of the periphery of bone-contacting surface 160. Rim 162, which is best illustrated in FIGS. 2C-2E, may be continuous or substantially continuous and follow along the entire periphery of bone-contacting surface, with the rim projecting substantially orthogonally and away from articular surface 170. With this configuration, the rim 162 of bone-contacting surface 160 may define the boundaries of a main contact area 164, the main contact area 164 surrounded by the rim, and the rim having a height that is greater than portions of main contact area adjacent the rim. The main contact area 164 may be configured to contact the resected femur 300, with the rim 162 configured to mate or lock with a peripheral recess 362 formed in the distal femur, as described in greater detail below.

The articular surface 170 may be patient-specific and/or population-specific. In other words, image data of the patient's knee using any suitable modality, such as computer tomography ("CT"), magnetic resonance imaging ("MRI"), ultrasound, and/or direct digitization, may be obtained. The image data may be utilized to model the geometry of the articular surface 170 of the femoral component 100. For example, all or part of the surface of the patient's modeled distal femur 300 may be utilized to create, for example via additive manufacturing or 3-D printing, articular surface 170 using appropriate materials. In other examples, the image data may be processed using a database of knee images, such as the Stryker Orthopaedics Modeling and Analytics ("SOMA") database, and an appropriate population-based articular surface 170 may be designed based on the relevant population, as opposed to being based on the particular individual patient. The term "population" as used herein may refer to any combination of relevant patient factors, including but not limited to, age group, sex, and ethnicity. It should be understood that, although it may be beneficial to create the geometry of articular surface 170 based on image data of the patient and/or other individuals in the patient's population, this is not a strict requirement of the invention.

Articular surface 170 functions to articulate with tibial component 200 and as such, material selection for articular surface 170 may be critical to long-term function of the implant system 10. In the past, femoral components of knee implants were generally formed of cast or forged metals in order to provide suitable strength to the component to prevent breakage, as the femoral component may undergo significant loading over time. In such prior systems, the metal femoral component would articulate with a plastic tibial component, which may result in sub-standard replication of healthy knee kinematics. In the illustrated embodiment, articular surface 170 is preferably formed of polyether ether ketone ("PEEK") or similar biocompatible engineering polymers, such as other materials in the polyaryletherketone ("PAEK") family. Such materials may be preferable because they may be relatively strong, have a modulus similar to native bone, have significant resistance to wear, have good biocompatibility, and may articulate well with polyethylene components described in greater detail below. As is described in greater detail below, the inventors have determined that forming articular surface 170 of femoral component 100 with a PAEK/PEEK surface results in enhanced performance compared to an identical system that otherwise includes a metal femoral articular surface. However, in order to provide the desired strength and fixation for femoral component 100, the bone-contacting surface 160 may be formed of metal. In particular, articular surface 170 may be a relatively thin layer that overlies the relatively thick bone-contacting surface 160. In some embodiments, the articular surface 170 may have a thickness of between about 2 mm and about 4 mm, or between about 20% and about 60% of the overall thickness of femoral component 100. Preferably, bone-contacting surface 102 is formed of a porous metal material, such as porous titanium, including Stryker's Tritanium® fixation surface. Porous materials may assist in ingrowth of bone of the native femur 300 into the pores of the femoral component 100 to assist in long-term fixation of the femoral component to the native bone.

Although FIG. 2C illustrates bone-contacting surface 160 and articular surface 170 of femoral component 100 as two separately formed components being joined together, that does not need to be the case. For example, bone-contacting surface 160 may be formed via additive manufacturing, with articular surface 170 formed by additive manufacturing on top of the bone-contacting surface, or by otherwise integrating the PAEK/PEEK into the pores of bone-contacting surface 160, for example by injection molding. If PAEK/PEEK is integrated into the pores of bone-contacting surface 160 to form articular surface 170, the porosity of regions of the bone-contacting surface may be designed to optimize the integration of PAEK/PEEK into those pores.

The metal substrate may include a relatively dense layer or region to limit flow of PAEK/PEEK material through the thickness of the substrate. This boundary layer or high density gradient blocks PEAK/PEEK intrusion into the intended bone ingrowth and/or bone interfacing surface. The boundary layer of high density gradient may also serve to help distribute forces through material into prepared bone that interfaces with the material. The process of bonding the PAEK/PEEK to the metal substrate may involve overmolding, heat staking with pressure, or other methods. Additionally, the surface of the substrate-facing PAEK/PEEK application can have a structure optimized to retain the applied bearing surface (e.g. interdigitation, adhesion, etc.) while the bone/biological tissue-facing surface can have a different structure optimized for fixation. Methods for preparing an implant component with PEEK are described in greater detail in U.S. Patent Publication No. 2014/0256229, the disclosure of which is hereby incorporated by reference herein. In other embodiments, a layer of PAEK/PEEK may be sprayed onto the outer surface of bone-contacting surface 160 to form a thin layer or film of PAEK/PEEK for articular surface 170.

An autonomous or semi-autonomous robotic device, such as a robotic arm with one or more end effectors, may be used to form some or all of the bone surfaces that contact the corresponding implant component. The robotic arm may be supplied with tool path data for autonomous bone preparation, and/or boundary data for semi-autonomous bone preparation. Areas of primary and secondary implant-to-bone contact may be discretely established. Different bone cutting parameters may be applied to the different discrete areas. For example, primary contact areas may be produced with greater precision and less dimensional clearance than secondary areas to guide and control bone fit. Secondary contact areas may be prepared with less than about 120 microns of intended clearance. Bone may be removed more rapidly from these secondary contact areas to help decrease the length of the procedure, while bone is removed more slowly from the primary contact areas to help ensure particularly high levels of precision. The tools and/or end effectors that may be used with such a robotic arm include, but are not limited to, burrs, ball or end mills, specialized saws and/or specifically profiled cutting bits. Some of the concepts described immediately above are described in additional detail in U.S. Pat. No. 9,427,334, the disclosure of which is hereby incorporated by reference herein.

Referring again to femoral component 100, the density of bone-contacting surface 160 may vary along main contact area 164, as well as along the depth between the bone-contacting surface 160 and articular surface 170. For example, it may be determined based on image data or any other suitable data the amount and variation of bone density of the portions of femur 300 that will be in contact with main contact area 164. During the additive manufacturing process, the density of bone-contact surface 160 may be intentionally varied by controlling the volume (e.g. porosity) of material in different areas of main contact area 164 so that, upon implantation, the different areas of main contact area substantially match the density of the native bone being contacted by each portion of main contact area. The density of the metal portions of femoral component 100 may also be varied so that the metal becomes denser farther away from bone-contacting surface 160, which may provide additional strength in locations that are less critical for bone-ingrowth. This printed structure may also incorporate engineered structures to control strength and rigidity such as struts or I-beams and notches or grooves. Preferably, the overall thickness of femoral component 100 between bone-contacting surface 160 and articular surface 170 is less than about 5 mm.

Figure 3A:
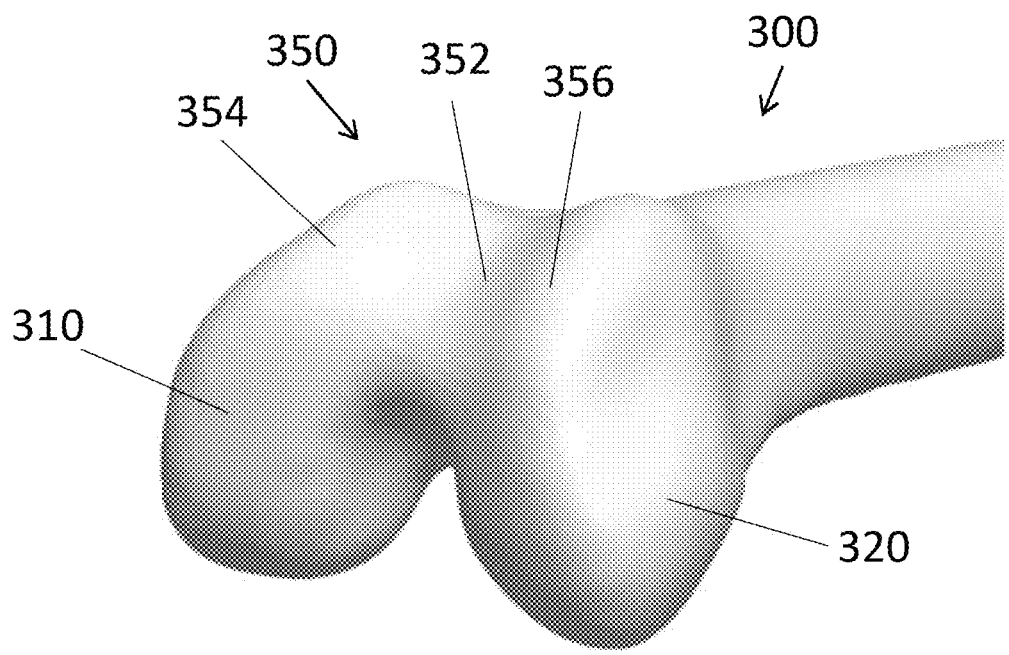
FIG. 3A is a perspective view of a native distal femur.
Figure 3B:
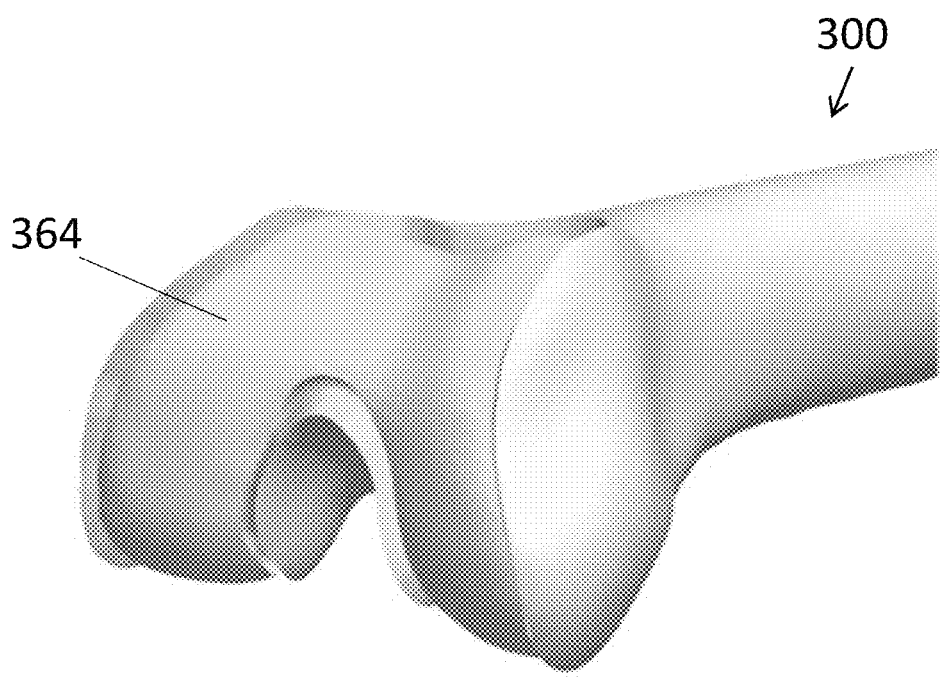
FIGS. 3B-C are various views of the native distal femur after being prepared for implantation of the femoral component of FIG. 1
Figure 3C:
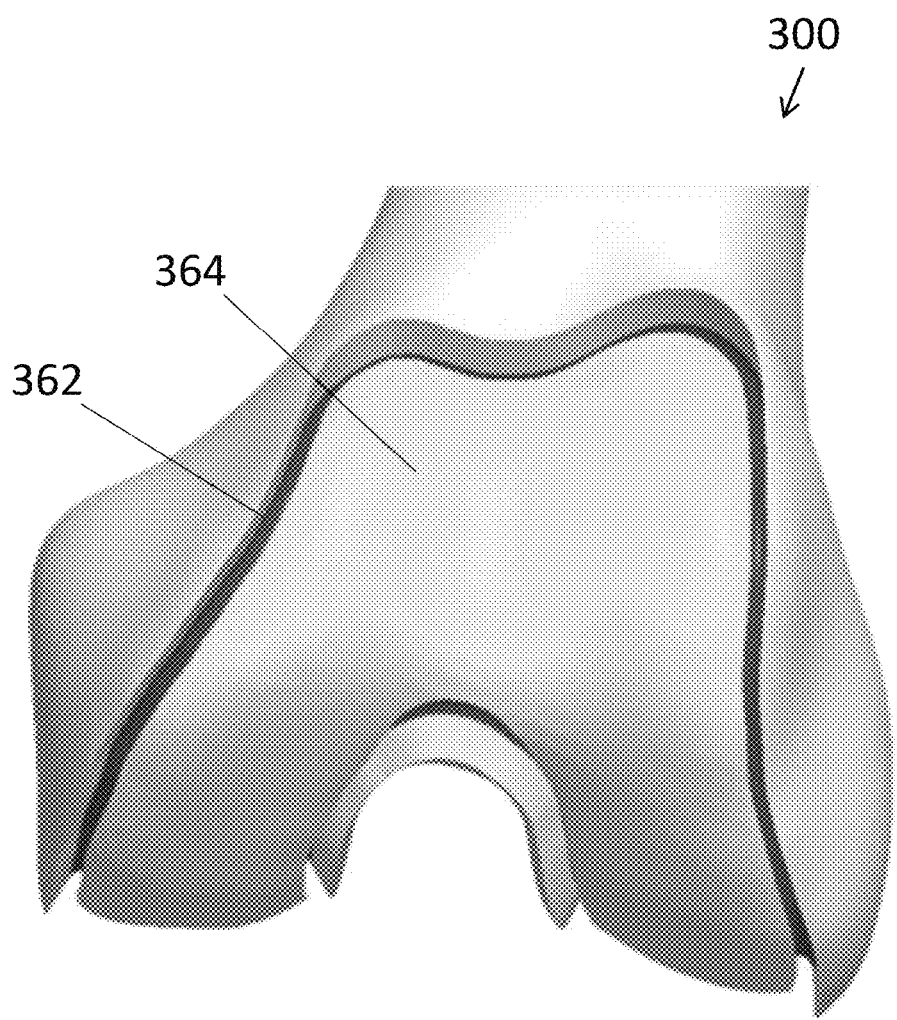

In other embodiments, if a femoral component 100 of uniform material is desired, the entire femoral component could be formed of porous PAEK/PEEK. The porous PAEK/PEEK could be formed in any desired gradient to allow, for example, for a relatively solid articulating surface 170 and a relatively porous bone-contacting surface 160. If PAEK/PEEK is used for both articular surface 170 and bone-contacting surface 160, reinforcing wire or a preformed endoskeleton could be used to help control dimensions and strengthen the rim of the femoral component, for example by fully enveloping the endoskeleton within the PAEK/PEEK through overmolding, or through secondary attachment via heat or ultrasonic staking, or other suitable methods FIGS. 3A-E illustrate femur 300, as well as the preparation of the femur for implantation of femoral component 100. As shown in FIG. 3A, femur 300 includes a medial condyle 310, lateral condyle 320, and a patellar guide portion 350 including groove 352 and raised portions 354, 356, substantially similar to those provided on femoral component 100. The native femur 300 is illustrated in FIGS. 3B-C after being prepared for implantation of the femoral component 100. In particular, data (e.g., geometry) regarding the bone-contacting surface 160 of femoral component 100 may be utilized, for example by a computer program operatively coupled to a robotic arm with one or more cutting tool attachments, to resect the distal portion of femur 300 to have a complementary shape to bone-contacting surface 160. FIG. 3B illustrates a main contact area 364 that has been created in femur 300 by resecting native bone such that main contact area 364 is substantially complementary to main contact area 164 of femoral component 100. For example, following implantation of femoral component 100 to femur 300, less than about 200 microns, preferably less than about 150 microns or less than about 120 microns of clearance exists between respective portions of main contact area 164 and main contact area 364.

Figure 3D:
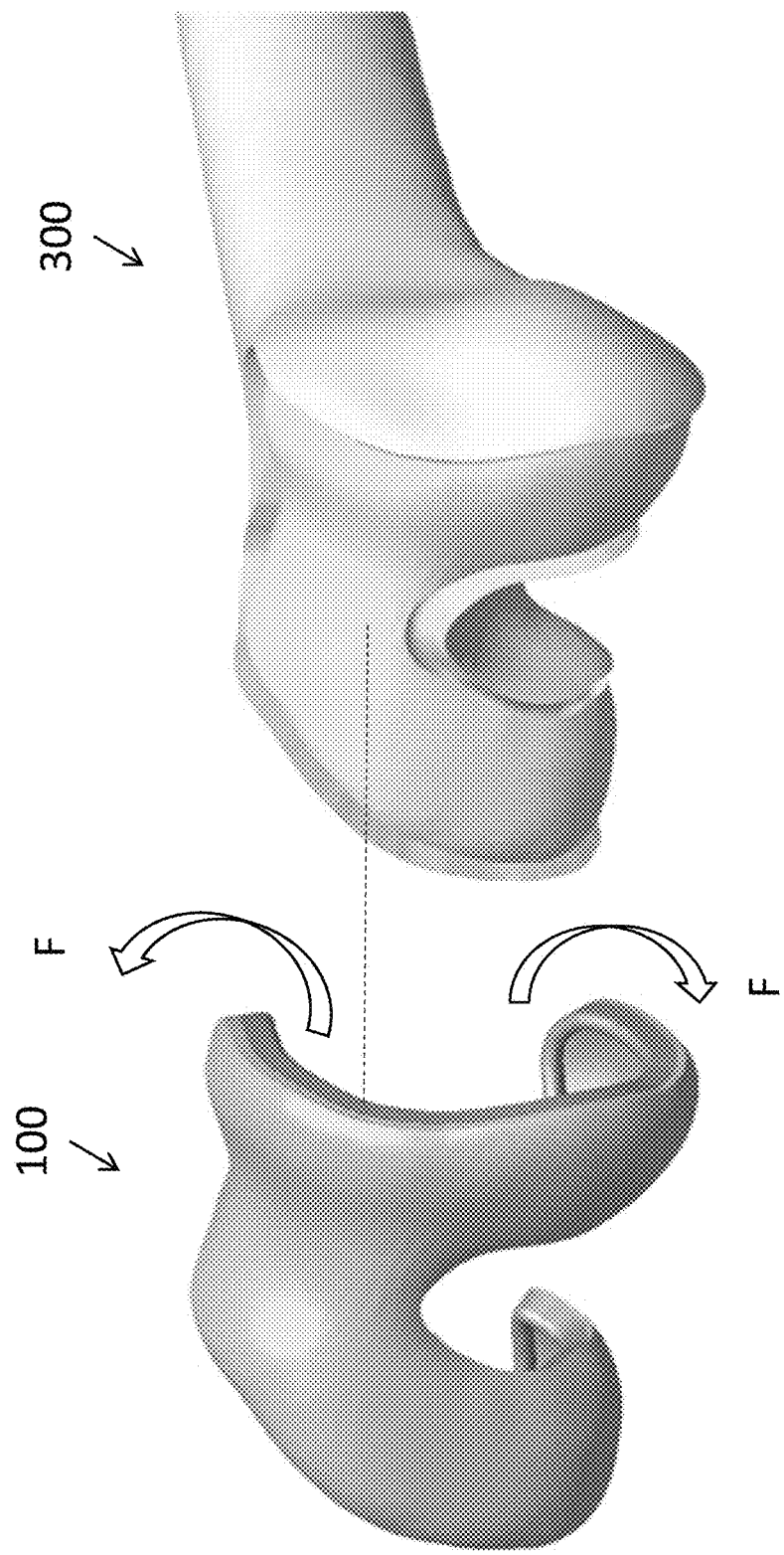
FIGS. 3D-E are perspective view of the femoral component of FIG. 1 being implanted onto the prepared femur of FIGS. 3B-C.
Figure 3E:
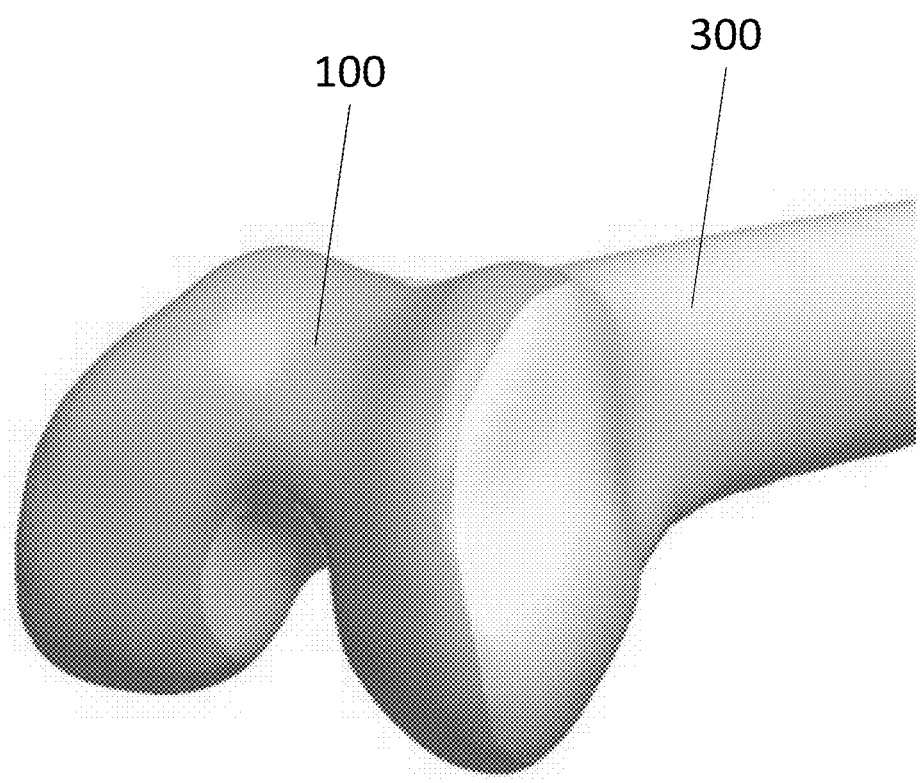

FIG. 3C best illustrates a peripheral recess 362 resected into the femur between native surfaces of the femur and main contact area 364. Peripheral recess 362 is generally complementary to the shape of peripheral rim 162 of femoral component 100. However, the geometry of peripheral recess 362 may be slightly offset compared to the geometry of peripheral rim 162 to help provide an interference fit to aid in initial fixation of femoral component 100 to femur 300. For example, as shown in FIG. 3D, after preparation of femur 300, femoral component 100 may be manually flexed in opposite directions F. For example, the medial condyle 110 and lateral condyle 120 may be grasped with one hand, and the patellar guide portion 150 may be grasped with the other hand, and the portions may be pulled away from another to increase the distance between the patellar guide portion and the condyles. Alternately or in addition, femoral component 100 may be flexed in the other direction, effectively hinging the femoral component 100 about groove 152 so that the articular surface 170 of the medial condyle 110 rotates a small amount toward the articular surface 170 of the lateral condyle 120. With the femoral component 100 flexed or stressed, the rim 162 of the femoral component may be inserted into the peripheral recess 362 of the femur. Once the rim 162 is positioned adjacent or at least partially within the peripheral recess 362, the stress may be released, allowing the femoral component to effectively "snap back" into place, forming an interference fit between the femoral component 100 and the prepared femur 300. The interference fit may provide a sufficient short term fixation between the femoral component 100 and the femur 300, with longer term fixation being facilitated by ingrowth of bone from the femur into the porous bone-contacting surface 160 of the femoral component. In some embodiments, the material properties of femoral component 100 may make it difficult to flex the component manually. Thus, in some embodiments, a separate tool may be provided to allow for precise and easy flexing of the femoral component 100, and the tool may also simplify the positioning and implanting process.

Figure 4A:
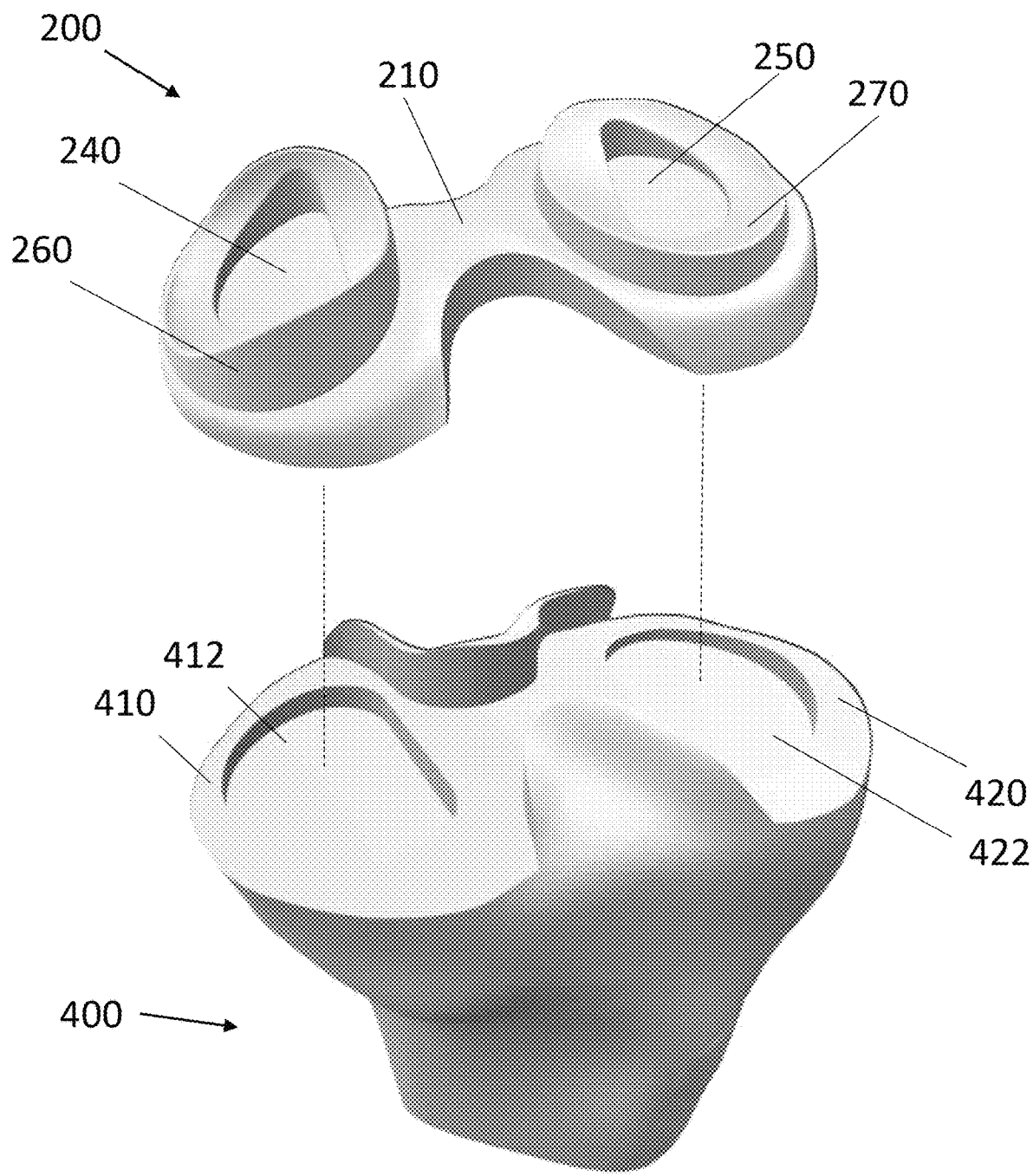
FIG. 4A is a perspective view of the tibial component of FIG. 1 being implanted onto a prepared proximal tibia.
Figure 4B:
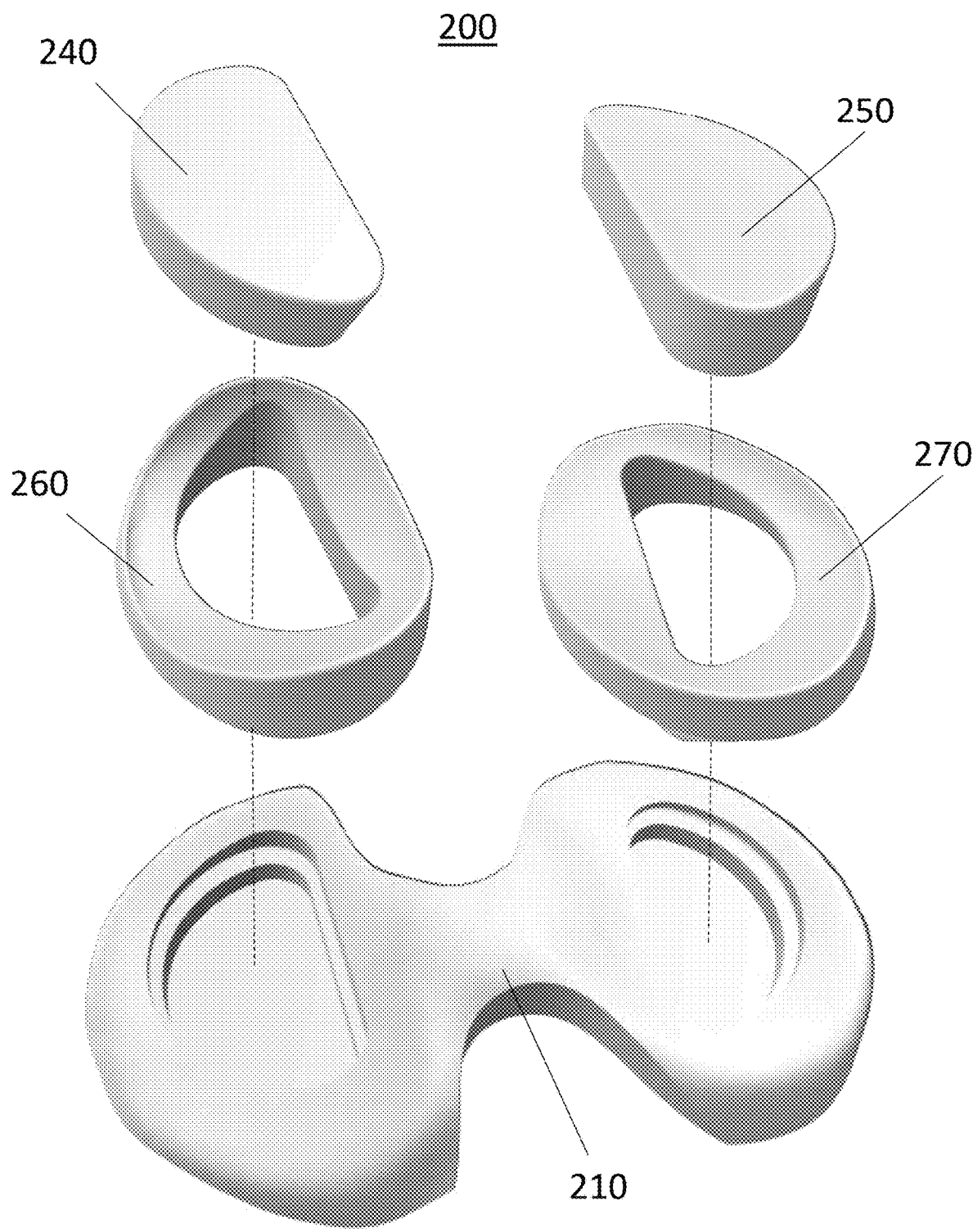
FIG. 4B is an exploded perspective view of the tibial component of FIG. 1.

Referring now to FIGS. 4A-B, tibial implant component 200 may be secured to the proximal end of tibia 400 and configured to replace the structure and function of the native tibial portion of the knee joint by any suitable method, including those described in greater detail below. Tibial component 200 may include a base 210, medial bearing or insert 240, lateral bearing or insert 250, medial meniscal component 260, and lateral meniscal component 270.

Figure 4C:
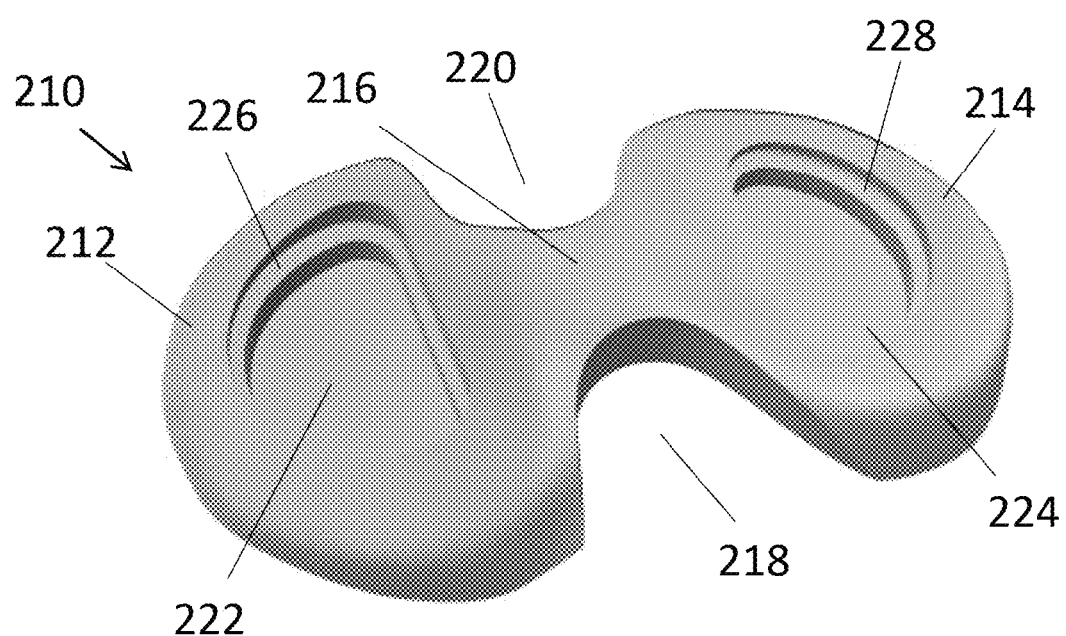
FIGS. 4C-D are top and bottom perspective views, respectively, of a base of the tibial component of FIG. 1.
Figure 4D:
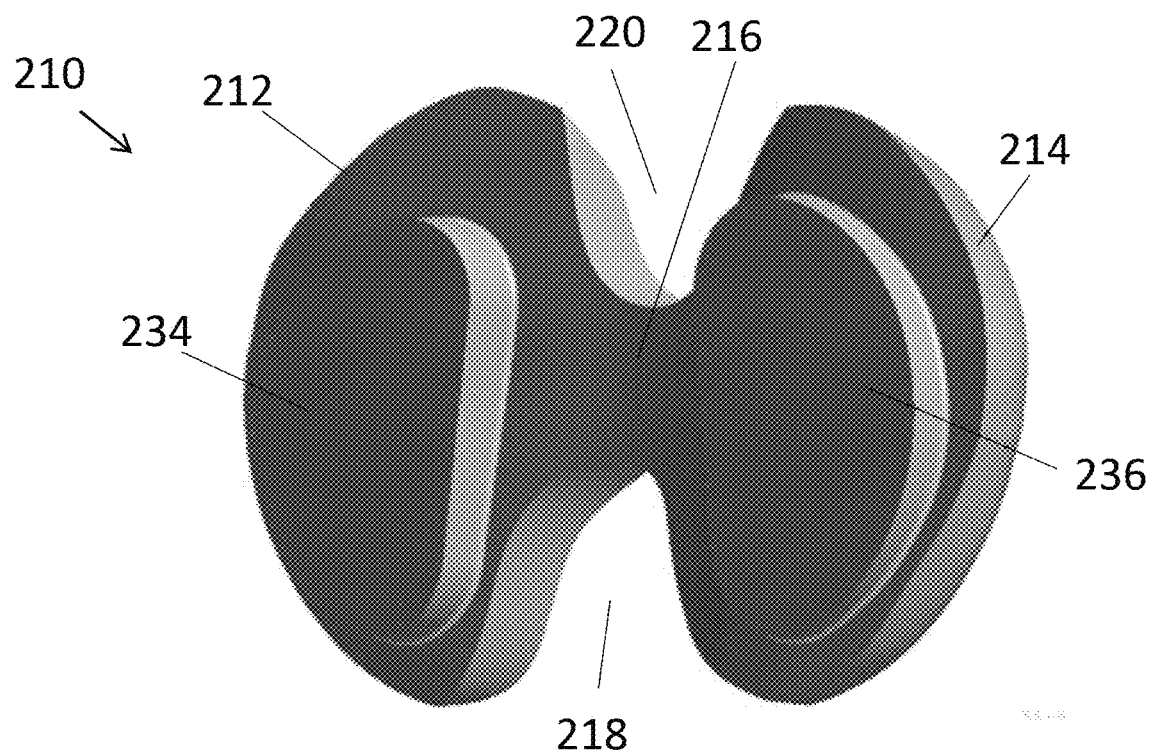

Top and bottom views of base 210 are illustrated, respectively, in FIGS. 4C-D. Base 210 may be configured to emulate the structure and function of portions of the proximal end of a healthy native tibia 400. Base 210 may include medial condylar portion 212, a lateral condylar portion 214, and a bridge 216 coupling the medial condylar portion to the lateral condylar portion. The distal or inferior surface of base 210 may include a "D"-shaped medial protrusion 234 and a "D"-shaped lateral protrusion 236, each having a smaller perimeter than the respective condylar portions 212, 214 and extending distally or inferiorly from the base 210. As is described in greater detail below, protrusions 234, 236 may facilitate both initial fixation and long-term fixation upon implantation into tibia 400, as well as assist with load distribution to the tibia.

Medial condylar portion 212 may be shaped to substantially match the shape of a healthy native tibial medial condyle 410, and lateral condylar portion 214 may be shaped to substantially match the shape of a health native tibial lateral condyle 420. Bridge 216 may connect the medial condylar portion 212 to the lateral condylar portion 214 near the center of each component in the anterior-posterior direction, leaving the posterior and anterior ends of the condylar portions not directly attached. In other words, an anterior notch 218 and posterior notch 220 may remain between the medial condylar portion 212 and lateral condylar portion 214. As is described in greater detail below, the position of bridge 216 and notches 218, 220 may assist in preserving a large amount of the native tibial eminence 430, helping to preserve a maximum amount of native bone, which may include native bone that serves as connection points to native cruciate ligaments.

Figure 4E:
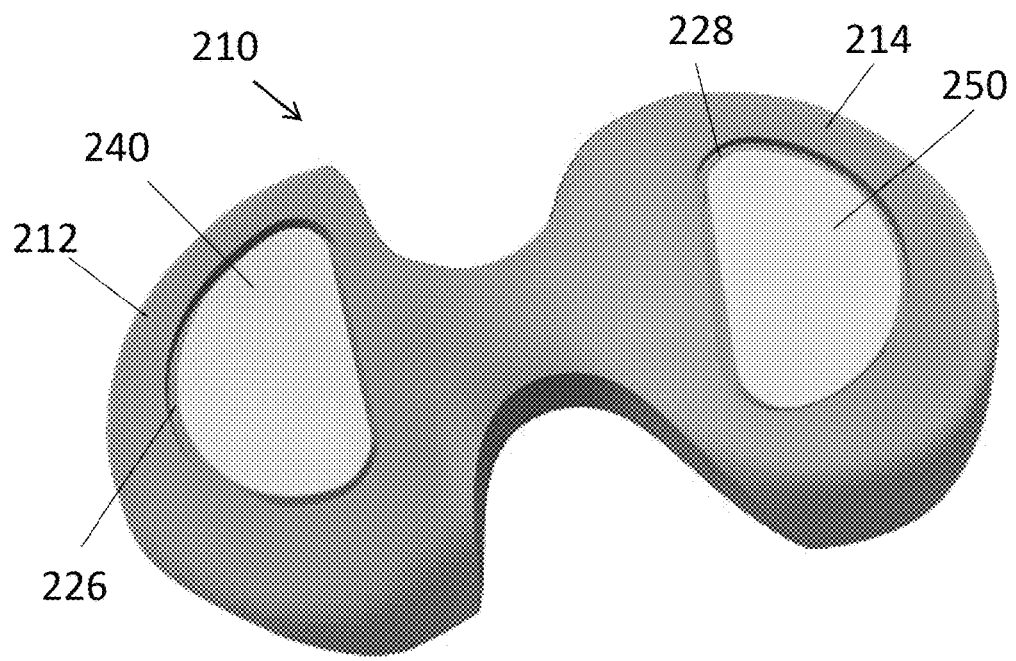
FIG. 4E is a top perspective view of bearing inserts assembled to the base of FIGS. 4C-D.

Base 210 may include various recesses to accept inserts 240, 250 and meniscal components 260, 270. Inserts 240, 250 may function as a replacement for natural cartilage, providing a surface against which articular surface 170 of femoral component 100 may articulate. Preferably, inserts 240, 250 each include a proximal or superior surface that is substantially flat or planar with minimal curvature. Referring to FIG. 4C, medial condylar portion 212 may include a substantially "D"-shaped recess 222 that matches the shape of medial insert 240. Similarly, lateral condylar portion 214 may include a substantially "D"-shaped recess 224 that matches the shape of lateral insert 250. When medial insert 240 and lateral insert 250 are inserted into recesses 222, 224, respectively, the distal or inferior surfaces of the inserts contact the proximal or superior surfaces of the recesses. Ledges 226, 228 may extend proximally or superiorly from recesses 222, 224, respectively, the ledges each extending along a perimeter in a "D"-shape. When the inserts 240, 250 are positioned within recesses 222, 224, respectively, the outer perimeters of inserts 240, 250 preferably snugly fit within and contact the interior side walls of ledges 226, 228 respectively. Further, when positioned within recesses 222, 224, inserts 240, 250 preferably extend proximally or superiorly so that proximal or superior surfaces of the inserts are at substantially the same height as the proximal or superior surfaces of medial and lateral condylar portions 212, 214, respectively. FIG. 4E illustrates base 210 with medial insert 240 and lateral insert 250 positioned within recesses 222, 224 respectively, with medial meniscal component 260 and lateral meniscal component 270 omitted. With the configuration described above, a gap between the perimeter of medial insert 240 and medial condylar portion 212, and a similar gap between the perimeter of lateral insert 250 and lateral condylar portion 214 is formed.

Figure 4F:
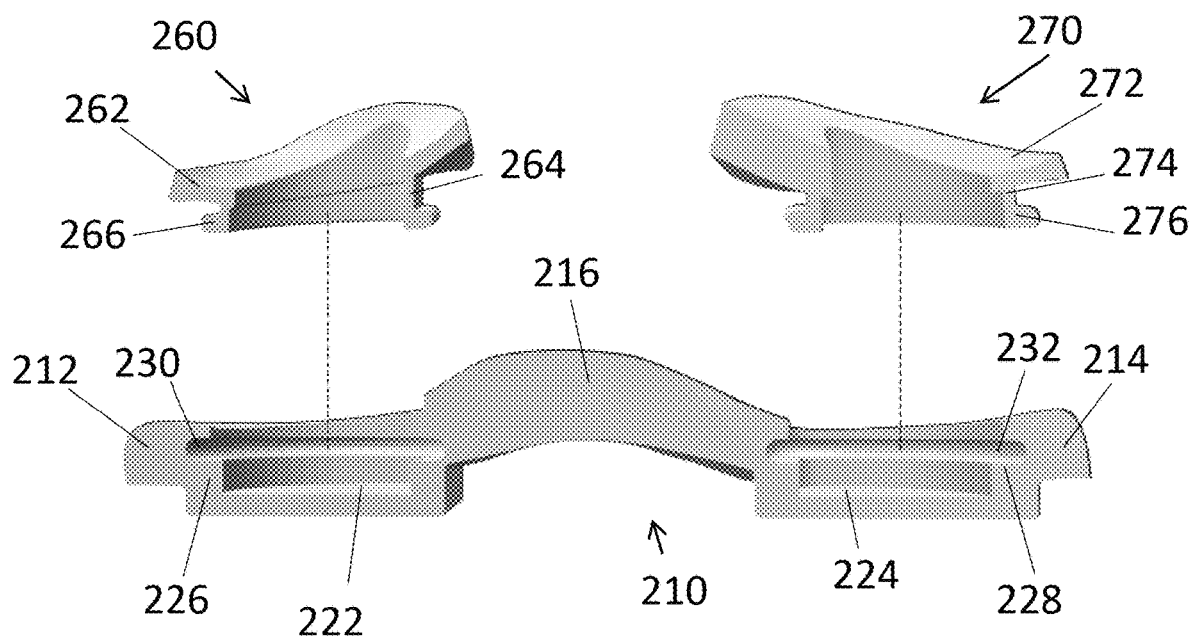
FIG. 4F is an exploded cross-section of the base of FIGS. 4C-D and prosthetic meniscal components.
Figure 4G:
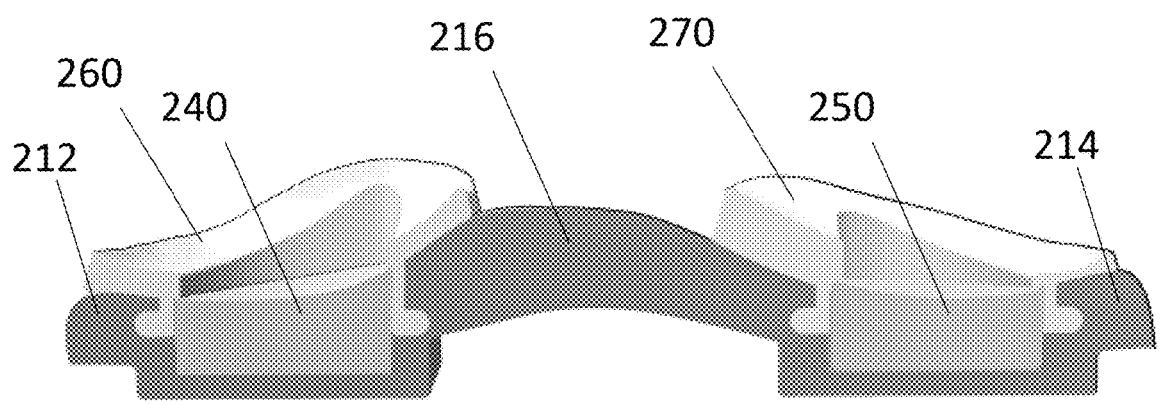
FIG. 4G is a cross-section of the tibial component of FIG. 1.

FIG. 4F shows base 210 and meniscal components 260, 270 disassembled in cross-section, with inserts 240, 250 omitted from the drawing. Recesses 222, 224 and ledges 226, 228 can be seen particularly well in FIG. 4F. In addition, a peripheral recess 230 may be formed directly superior of ledge 226 in medial condylar portion 212, with the peripheral recess being undercut so that a portion of the medial condylar portion overlies the peripheral recess. Peripheral recess 230 may be substantially continuous and extend along the entire circumference of ledge 226, forming a general "D"-shape. Lateral condylar portion 214 may include a peripheral rim 232 having substantially the same characteristics as peripheral rim 230, with the main exception being that it is positioned on the lateral condylar portion of the base 210. Peripheral recesses 230, 232 may function to help secure meniscal components 260, 270 to base 210, respectively. In particular, medial meniscal component 260 may include a main contact surface 262 for contacting and supporting portions of medial condyle 110 of femoral component 100 during articulation of the femoral component relative to the tibial component 200—particularly at the extremes of the joint's range of motion. As should be understood and as is described in greater detail below, the meniscal components 260, 270 function to faithfully replicate the function of healthy native menisci. The portion of main contact surface 262 closer to bridge 216 may extend a greater distance in the proximal direction than the portion of main contact surface farthest away from the bridge. In other words, the height of main contact surface 262 generally decreases in a direction away from the center of base 210 so that the meniscal component has a wedge shape. Medial meniscal component 260 may also include a relatively thin side wall 264 extending proximally from main contact surface 262, the side wall extending substantially continuously along a perimeter of the medial meniscal component. When medial meniscal component 260 and medial insert 240 are assembled to base 210, as shown in FIG. 4G, the side wall 264 is positioned through the gap between the medial insert and the medial condylar portion 212 mentioned above in relation to FIG. 4E. Referring again to FIG. 4F, the proximal end of side wall 264 may include a peripheral rim 266 extending radially outward therefrom. When assembled, as shown in FIG. 4G, the peripheral rim 266 may snap fit, press fit, or otherwise fit into peripheral recess 230 to help medial meniscal component 260 remain coupled to base 210. The snap fit or press fit may be facilitated, at least in part, by the combined geometry of medial meniscal component 260 and medial insert 240 positioned within the meniscal component. Lateral meniscal component 270 may have similar features and engage similarly with lateral condylar portion 214. Without reiterating in great detail, lateral meniscal component 270 may include a main contact surface 272 adapted to engage with the lateral condyle 120 of femoral component 100. Lateral meniscal component 270 may also include a side wall 274 that at least partially surrounds lateral insert 250, and a peripheral rim 276 that fits within peripheral recess 232 when the lateral meniscal component and lateral insert are both assembled to lateral condylar portion 214 of base 210. It should be understood that medial meniscal component 260 and lateral meniscal component 270 do not need to be mirror images of one another—and in fact it may be preferable for the medial and meniscal components to have different geometries. In other words, the cross-section profile shape of meniscal components 260, 270 may vary regionally along the overall "D"-shape, including the height, the width, and the cross-sectional shape, with the variations being suited to the position and intended function of the particular meniscal component.

As with femoral component 100, the particular materials chosen for the various elements of tibial component 200 are of particular importance to produce the desired characteristics for fixation and replication of function of the healthy knee. Preferably, base component 210 is formed of a metal or metal alloy, which may help provide structural stability to the tibial component 200. In one example, base 210 is formed of titanium, such as porous titanium, including Stryker's Tritanium® fixation surface. The level of porosity of titanium in base 210 may vary based on position and density of the native tibia 400. For example, referring to FIG. 4D, the proximal surfaces of both protrusions 234, 236, as well as the inferior surface of the remainder of base 210, may include porous titanium. The distribution of the pores in those inferior faces may be designed so that the density of the titanium substantially matches the bone density of the portions of the native tibia in contact with the titanium. As described above in connection with femoral component 100, the density of the native tibia 400 may be determined via imaging, with varied density of the titanium being created via additive manufacturing to substantially match the native bone density in order to promote bone growth into the pores to facilitate long-term fixation. The porosity of the titanium of base 210 may decrease in the proximal direction toward the proximal face of base 210. In other words, the proximal or superior portions of base 210 may have few or no pores, resulting in a relatively high density to mirror the relatively high density of the tibial cortex. The side walls of protrusions 234, 236 and the side walls of the remainder of base 210 may similarly be formed of relatively high density titanium to add structural strength to the recesses 222, 224 that will contain tibial inserts 240, 250. These side wall surfaces may serve as initial implantation fixation features. Preferably, only the distalmost aspects adjacent to the horizontal surfaces are porous. Struts, I-beams, crossbars or other structural reinforcing elements may be incorporated within the side walls or under the base of the recesses 222, 224, to provide sufficient device strength.

Figure 4H:
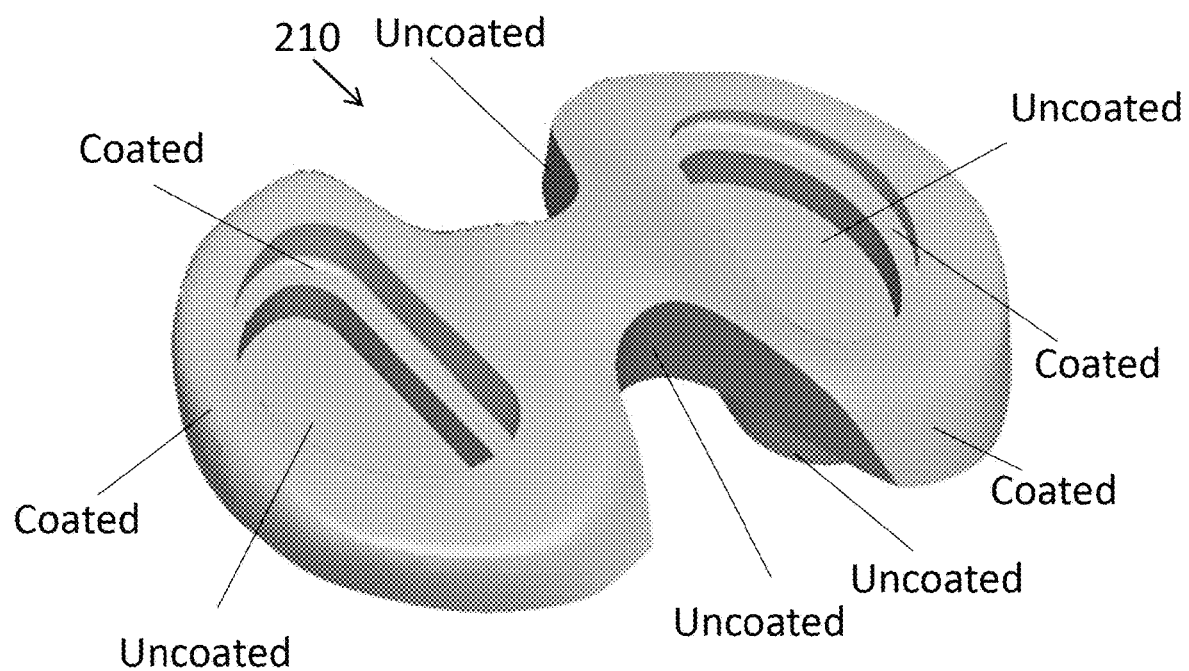
FIG. 4H is a top perspective view of the base of FIGS. 4C-D.

It should further be understood that the general shape of base 210 may be designed in a patient-specific or population specific manner based on image data, with the goal that upon implantation, the outer surfaces of base 210 mimic the shape of a healthy superior tibial cortex. In some embodiments, it may be preferable to cover or coat the surfaces of base 210 that are exposed after implantation with a non-metallic material. For example, after implantation, the side walls of base 210 are exposed, excluding the side walls defining notches 218, 220, which would be in direct contact with portions of the tibial eminence 430. In addition, after implantation, the proximal or superior face of base 210, excluding portions covered by inserts 240, 250 and/or meniscal components 260, 270, will also be exposed. It may not be preferable to have exposed metallic surfaces, as those metallic surfaces may damage or irritate soft tissues in contact with such exposed surfaces. Thus, as shown in FIG. 4H, the exposed surfaces may include a coating such as a PAEK/PEEK coating, which may be added to the titanium core of the uncoated surfaces in substantially the same manner as described above for femoral component 100. However, such a coating is not strictly necessary, and alternately other coatings that are soft tissue-friendly and non-irritating may be used instead of or in addition to PAEK/PEEK. Still further, other satisfactory approaches may include polishing the exposed metal surfaces to reduce any irritation between soft tissues and the exposed metal surface. There also may be regions of intended articulation on the superior or proximal surface of base 210 that may be similarly polished and coated with a wear-resistant surface treatment.

Medial insert 240 and lateral insert 250 are preferably formed from a low friction and high-strength material, such as polyethylene, including ultra-high molecular weight polyethylene ("UHMWPE"). For example, medial insert 240 and lateral insert 250 are preferably formed of X3® polyethylene bearing material produced by Howmedica Osteonics Corp. Alternately, other highly wear resistant and sufficiently strong polyethylene bearing materials may be used for medial insert 240 and lateral insert 250. The inventors have found that articulation of femoral component 100 against inserts 240, 250, particularly when the femoral component articulation surface 170 is PAEK/PEEK and the articulation surface of inserts 240, 250 is substantially flat and formed of UHMWPE, produces extremely small wear in the prosthetic components. The flat polyethylene inserts 240 and 250 replicate native cartilage contact surfaces with high fidelity. However, at the extremes of knee articulation (e.g. deep flexion or extension), the flat inserts 240, 250 alone may poorly replicate native meniscal functionality. Meniscal components 260, 270 are able to replicate function of the native menisci. Forming meniscal components 260, 270 from polyurethane may be particularly helpful in mimicking the function of native menisci, as described in greater detail in U.S. Pat. No. 6,994,730, the disclosure of which is hereby incorporated by reference. Although polyurethane may be the preferred material, other materials including hydrogels or silicones, and the materials may be homogenous, reinforced, or even graded. In other words, the geometry of meniscal components 260, 270, and material properties of polyurethane of the meniscal components, help to ensure that as the joint undergoes articulation at the extremes of the joint's range of motion, the meniscal components will displace and compress to assist in maintaining appropriate contact and stability between the articular surface 170 of femoral component 100 and the tibial component 200 via the meniscal components. The particular geometries of meniscal components 260, 270 may be based, at least in part, on the geometries of the native menisci as they undergo loading in flexion and extension. Elastic deformation of meniscal components 260, 270 may be controlled variably. Methods for variably controlling the elastic deformation, specific to knee motion arcs and loading, may be specified, for example, based on patient-specific soft tissue constraints, resilience factors, and projected life-style and/or activity factors.

In one embodiment, meniscal components 260, 270 may be of single durometer with variable cross-section. This embodiment may feature large surface areas and thicker cross-sections in areas required to support high loads. The cross-section may be reduced at areas expected to support lower loads and where greater levels of elastic deformation are expected to be required. The durometer may be greater in patients that would benefit from higher degrees of stabilization or shock absorption from meniscal components 260, 270. On the other hand, the durometer may be decreased in patients expected to undertake low impact, high mobility tasks and/or activities. As noted above, it should be understood that for this embodiment and others, the shapes of the meniscal components need not be mirror images of one another.

In another embodiment, meniscal components 260, 270 may be of multiple durometer with variable cross-section. This embodiment may feature large surface areas and cross-sections that are thicker and have higher durometer in areas required to support high loads. The cross-section and durometer may be reduced in areas where lower loads and greater levels of elastic deformation are expected to be required. The durometer of specific zones of the components may be increased for patients expected to require greater degrees of stabilization or shock absorption from meniscal components 260, 270. On the other hand, the durometer of specific zones may be decreased in patients expected to undertake low impact, high mobility tasks and/or activities. Combinations of durometers may be molded and overmolded to provide the desired variations in material properties for different loading conditions at different arcs of motion and with different activities. If appropriate, these geometries could also be machined or cut (cryo-cut or otherwise) from cast or molded blocks of material with desired properties. Such source material may have specially graded properties.

In a further embodiment, meniscal components 260, 270 may be overmolded and include an endoskeleton. In this embodiment, meniscal components 260, 270 may include an endoskeleton in the form of an oriented fiber, wire, substantially low density additive manufactured metal, and/or high durometer polymer. The endoskeleton may be overmolded with large surface areas, thicker cross-sections, and higher durometer in areas expected to support high loads. The components may incorporate reinforcing features such as wires or cables or netting to aid in supporting hoop and radial stresses. The cross-section and/or the durometer of the endoskeleton may be reduced in areas expected to support lower loads and where greater levels of elastic deformation are expected to be required. The cross-sections and/or durometers in specific zones of the endoskeleton may be increased in patients expected to require greater degrees of stabilization or shock absorption by the meniscal components 260, 270. On the other hand, the cross-sections and/or durometers in specific zones of the endoskeleton may be reduced in patients expected to undertake low impact, high mobility tasks and/or activities. Combinations of endoskeleton cross-section and/or durometers may be molded and/or overmolded to provide desired variations in composite material mechanical properties for different loading conditions at different arcs of motion and with different activities.

It should further be understood that although tibial component 200 is shown with notches 218, 220, in other embodiments these notches may be omitted. For example, base 210 could include material where notches 218, 220 are shown in the figures. That material could include porous structures that could facilitate attachment and/or fixation surfaces for ligaments, such as the ACL or PCL. It may not be desirable to attach a ligament directly to base 210 immediately after implantation, as forces applied to the base by the ligaments may promote destabilization. However, after base 200 had time to properly fix to the native tibia, the porous structures where notches 218, 220 are shown could be suitable for soft tissue ingrowth and/or mechanical means for tissue fixation, such that once the base is sufficiently stable, the ACL and/or PCL could be directly attached to the base (as opposed to being attached to the native bone that would otherwise protrude through the notches). Such mechanical means could include, for example, threaded features, alligator clamps, etc.

Figure 5A:
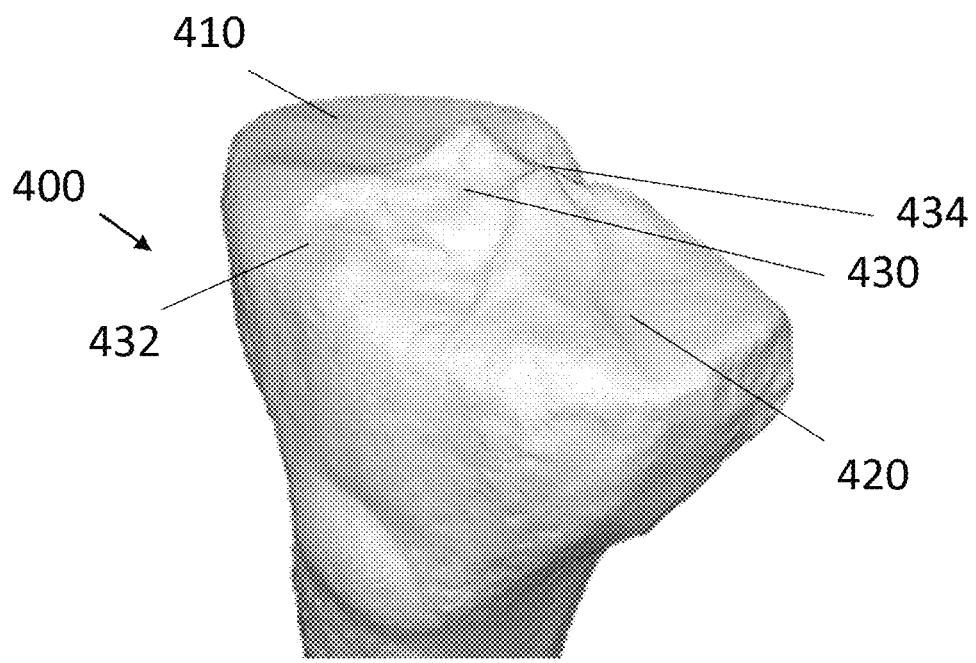
FIG. 5A is a top perspective view of a native proximal tibia.
Figure 5B:
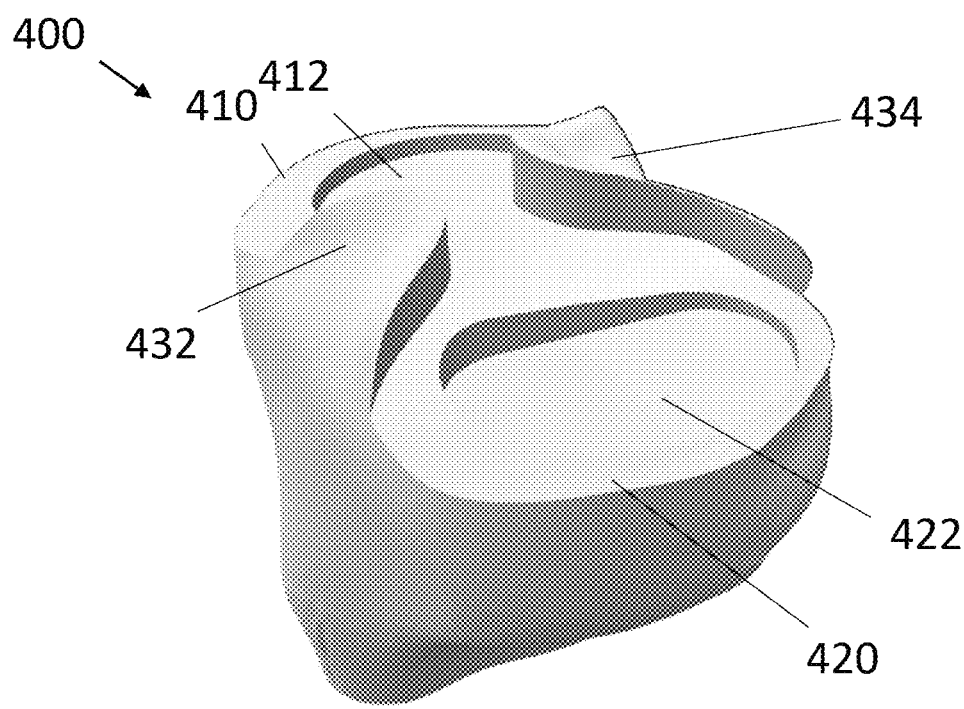
FIG. 5B is a top perspective view of the native proximal tibia after being prepared for implantation of the tibial component of FIG. 1.

FIG. 5A illustrates the proximal end of native tibia 400 prior to preparation for implantation. Tibia 400 includes a medial condyle 410, a lateral condyle 420, and a tibial eminence 430 interposed between the medial and lateral condyles. Tibial eminence 430 may include an anterior portion 432, which serves as the attachment site for the ACL, and a posterior portion 434, which serves as an attachment site for the PCL. Tibia 400 is illustrated in FIG. 5B after being prepared to receive tibial component 200. As a general matter, it is often preferable to retain as much healthy bone stock as possible. In particular, it is preferable to retain the posterior portion 434 and anterior portion 432 of tibial eminence 430, particularly if the PCL and ACL, respectively, are to be maintained intact after the implantation. Even if the PCL and/or ACL is not retained, it may still be preferable to spare the posterior portion 434 and anterior portion 432 of tibial eminence 430. A generally planar surface may be resected into the remaining proximal face of tibia 400, with the medial condyle 410 and lateral condyle 420 being resected. In addition, a substantially "D"-shaped recess 412 may be formed in medial condyle 410, and a substantially "D"-shaped recess 422 may be formed in lateral condyle 420. The resulting shape of the tibial resection may be thought of as a "figure eight" shape.

Figure 5C:
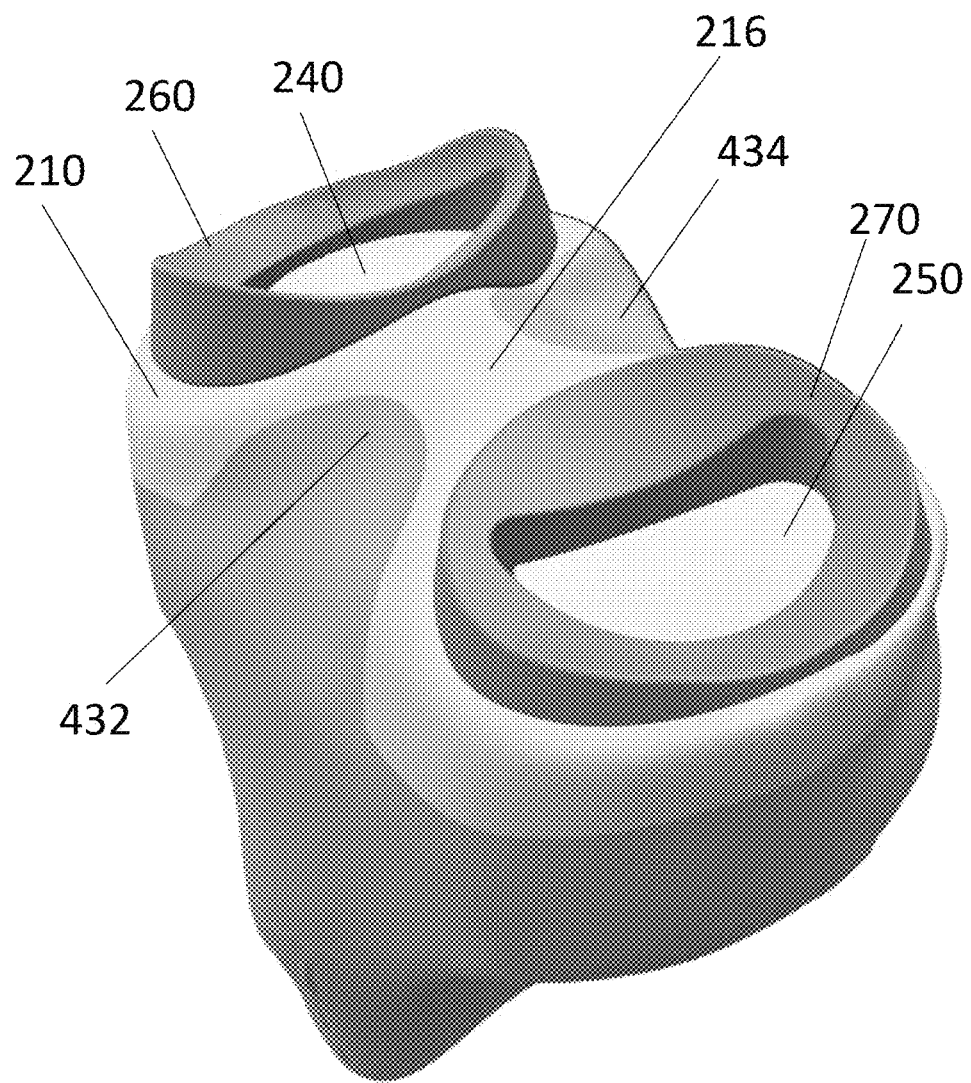
FIG. 5C is a top perspective view of the tibial component of FIG. 1 implanted onto the prepared tibia of FIG. 5B.

In order to form the relatively intricate resections in proximal tibia 400, a robotic cutting tool is preferably employed. Similar to the method described for resecting native femur 300, the geometry and/or design of tibial component 200 may be uploaded into a computer in order to create a robotic resection plan so that the shape of the resected tibia corresponds closely or identically with the corresponding features of tibial component 200. For example, recesses 412 and 422 correspond in shape to projections 234, 236 respectively. Thus, if projections 234, 236 had shapes other than a "D"-type shape, the recesses 412, 422 formed in proximal tibia 400 would have correspondingly different shapes. Referring to FIGS. 4A and 5C, once tibia 400 is prepared for implantation, base 210 may be implanted onto the proximal tibia. In particular, projection 234 may be seated in recess 412 and projection 236 may be seated in recess 422. As noted above, distal surfaces of projections 234 and 236 may include porous titanium, preferably with densities that closely match the native bone with which they engage, in order to facilitate bone growth from native tibia into the pores of the distal surfaces of projections 234, 236. In addition to this long term fixation, the engagement of projections 234, 236 with recesses 412, 422 may also facilitate initial fixation, for example via frictional engagement which, due to the interlocking nature of the engagement, may also help prevent rotation or other movement of tibial component 200 with respect to tibia 400. Still further, the projections 234, 236 may help concentrate applied loads toward the center of each respective condyle 410, 412.

The remaining distal or inferior surfaces of base 210—other than projections 234, 236—may further facilitate long term fixation with bone ingrowth from the proximal tibia into porous metal at the distal surfaces of the base. In addition, upon implantation, anterior tibial eminence 432 closely engages with the surfaces of tibial component 200 that form notch 220, and posterior tibial eminence 434 closely engages with the surfaces of tibial component 200 that form notch 218. The engagement of the resected surfaces of anterior eminence 432 and posterior eminence 434 with bridge 216 and other surfaces of base 210 help to provide additional initial fixation with the interlocking fit. As noted above, base 210 is preferably designed so that, after implantation, there is smooth transition between the remaining outer cortex of the tibia with the exposed outer surfaces of base 210. Although inserts 240, 250 and meniscal components 260, 270 are preferably all assembled to base 210 prior to implantation, it should be understood that those components may be assembled after the base is seated on the resected tibia 400.

Figure 6A:
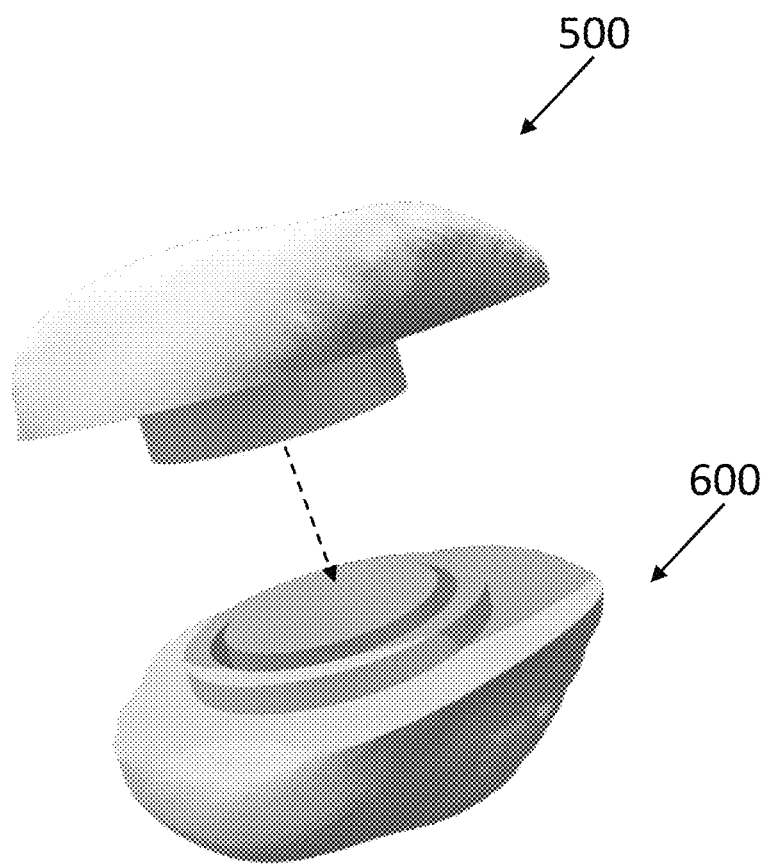
FIG. 6A is a perspective view of a prosthetic patellar component separated from a prepared native patella.
Figure 6B:
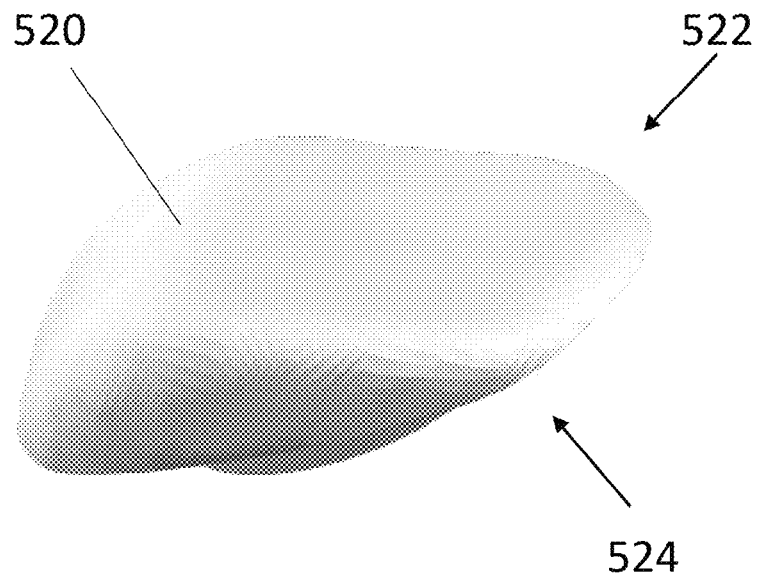
FIGS. 6B-C are top and bottom perspective views of a body of the patellar component of FIG. 6A.
Figure 6C:
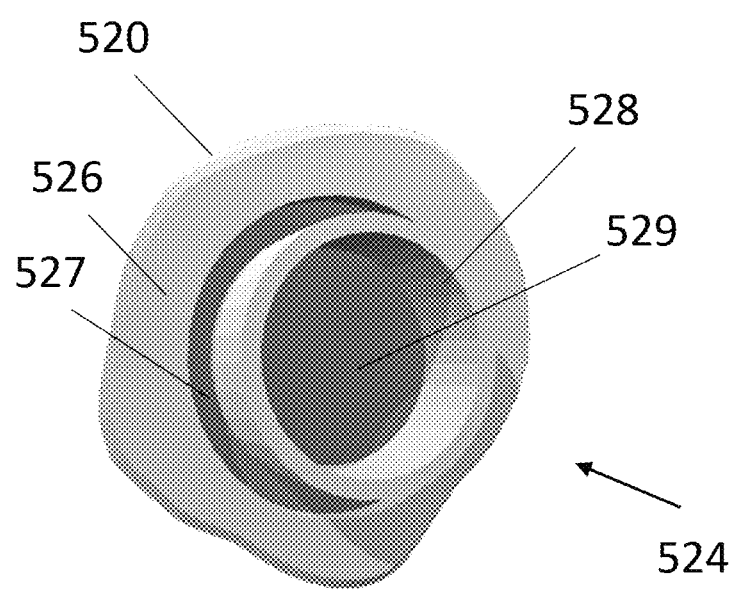

Although implant system 10 is shown as including a femoral component 100 and tibial component 200, a corresponding patellar component 500 may be provided with the implant system. One example of a patellar component 500 adjacent a prepared native patella 600 is illustrated in FIG. 6A. Patellar component 500 may include a rigid body 520, shown in different views in FIGS. 6B-C. Body 520 may include a first surface 522 that will face the knee joint and a second surface 524 that couples to the prepared native patella 600. As shown in FIG. 6C, the second surface 524 may include a main contact surface 526, an peripheral recess 527 radially inward of the main contact surface, a peripheral rim 528 (which may be cylindrical) protruding beyond the main contact surface and the peripheral recess, and a central recess 529. Body 520 could be formed of a strong metal, such as titanium. Alternately, body 520 could be a formed of porous titanium with similar considerations as described above for base 210 of tibial component 200 and/or bone-contacting surface 160 of femoral component 100.

Figure 6D:
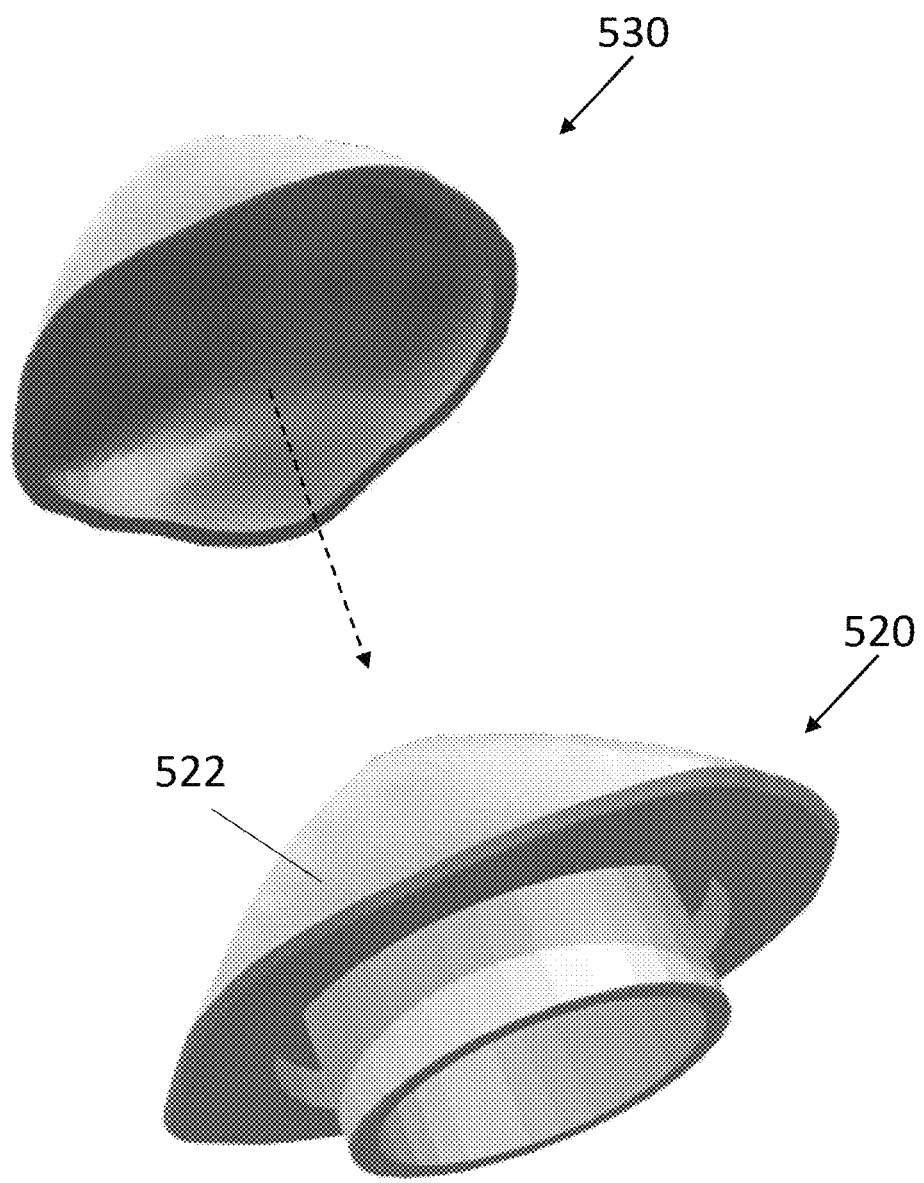
FIG. 6D is a perspective view of an articular surface of the patellar component of FIG. 6A separated from the body of the patellar component.

Patellar component 500 may include an articular surface 530 in addition to body 520, as shown in FIG. 6D. Although in FIG. 6D, articular surface 530 is illustrated as a separate component that is mated with the first surface 522 of body 520, it should be understood that the articular surface may otherwise be applied to body 520, similar to the description above of articular surface 170 of femoral component 100 being applied to bone-contacting surface 160. In one embodiment, articular surface 530 may be formed of a PAEK/PEEK material. If such a patellar component 500 is provided, it may be preferable to modify femoral component 100. For example, groove 152, which forms a portion of the patellofemoral joint, may include a distinct material, such as polyethylene, including UHMWPE. For example, groove 152 may be formed so that the surface presented at and along groove 152 is formed of X3® polyethylene bearing material produced by Howmedica Osteonics Corp., although other similar wear resistant and strong materials may be suitable. With such a configuration, the PAEK/PEEK articular surface 530 of patellar component 500 is adapted to articulate with the polyethylene surface of groove 152. The benefits described above of a PAEK/PEEK articular surface articulating against UHMWPE surface with respect to femoral component 100 and tibial component 200 may apply with equal force to a patellar component 500 articulating with femoral component 100. However, it should be understood that in other embodiments, articular surface 530 of patellar component 500 may be formed of UHMWPE or other similar materials, with groove 152 of femoral component including a PEAK/PEEK material to articular with the articular surface of the patellar component.

Figure 6E:
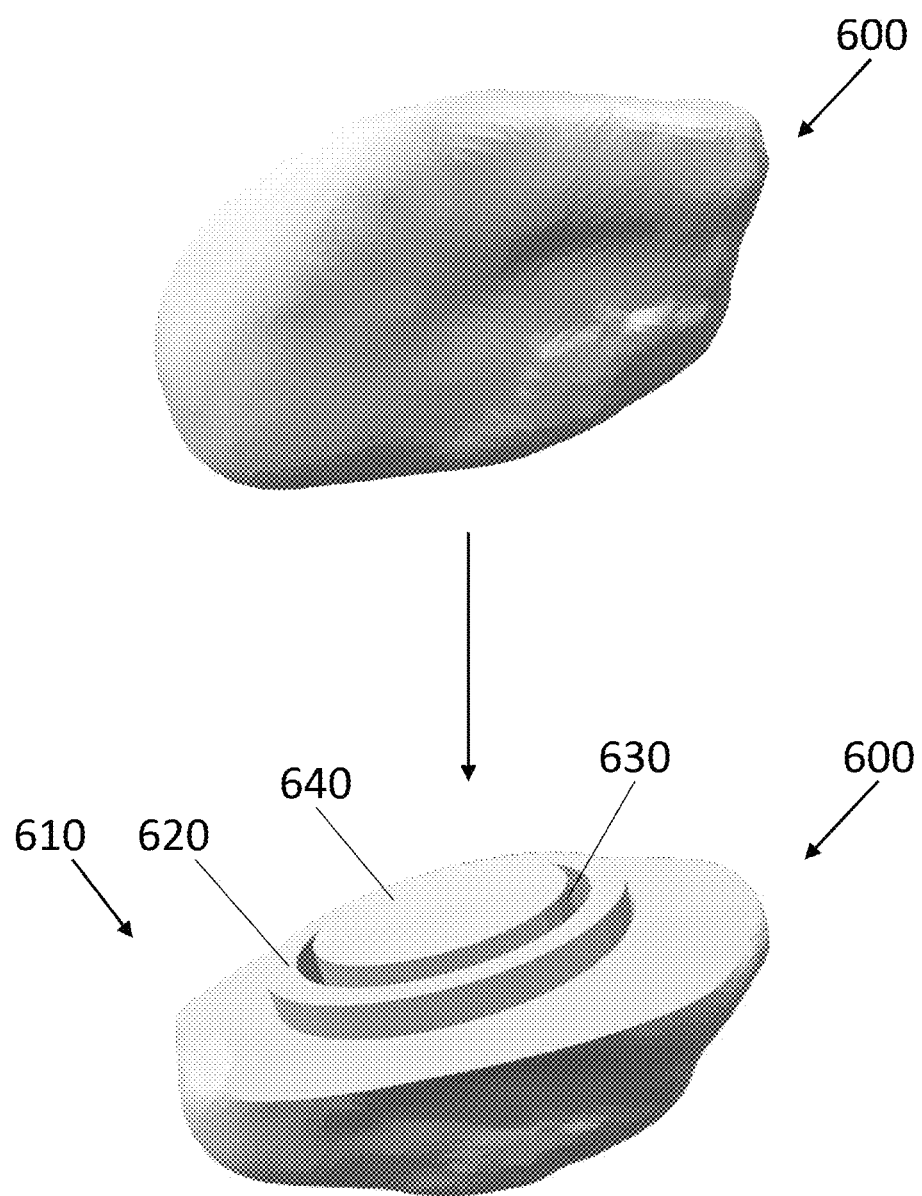
FIG. 6E is a perspective view of the native patella before and after preparation to accept the patellar component of FIG. 6A.
Figure 6F:
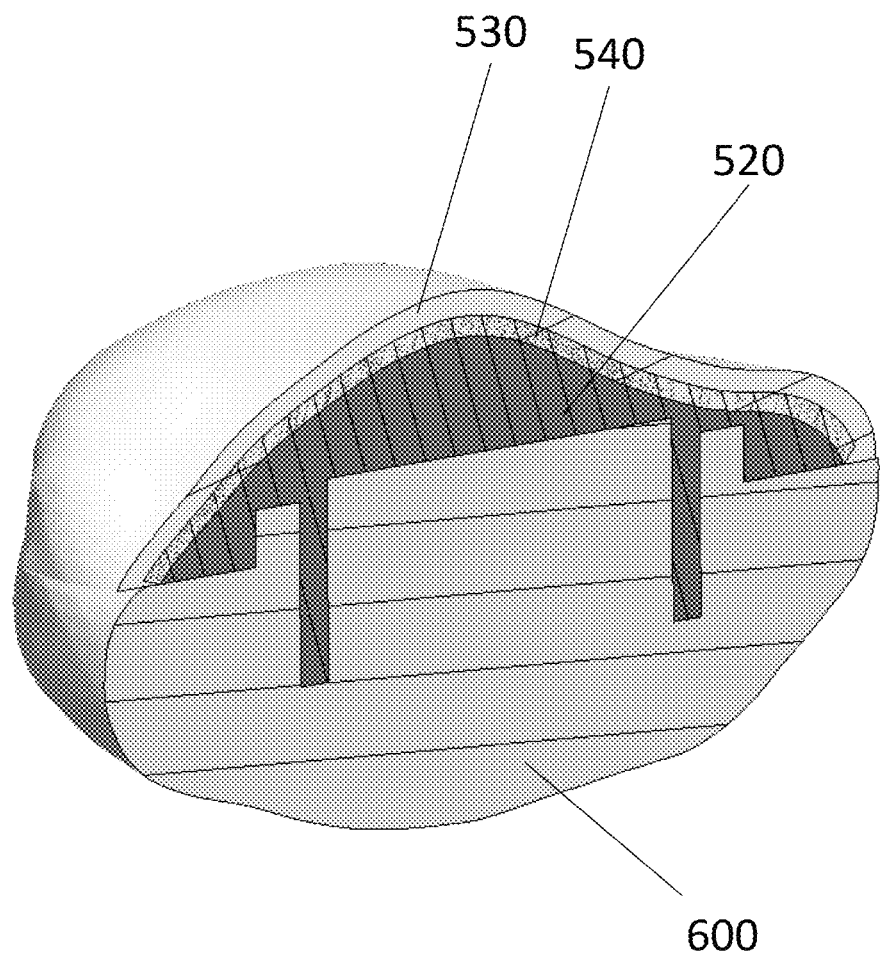
FIG. 6F is a cross-section of the patellar component of FIG. 6A implanted onto the prepared patella.

FIG. 6E illustrates a native patella 600 prior to preparation (at the top of FIG. 6E) and after preparation (at the bottom of FIG. 6E) to accept patellar component 500. An implant-facing surface 610 may me created in native patella 600 manually, or semi-autonomously or autonomously with the aid of a robotic tool similar to those described above. Implant-facing surface 610 may have complementary features to the second surface 524 of patellar component 500. For example, implant-facing surface 610 may include an outer peripheral rim 620 adapted to be positioned within peripheral recess 527. A peripheral recess 630 may be positioned radially inward of peripheral rim 620, the peripheral recess 630 adapted to receive the peripheral rim 528 of patellar component 500 therein. A central protrusion 640 may be positioned radially inward of peripheral recess 630, the central protrusion 640 sized and shaped to be received within central recess 529 of patellar component 500. Some or all of the surfaces of patellar component 500 in contact with native patella may include pore density so that the surfaces have a similar density to the native bone, with the pores facilitating bone ingrowth for long term fixation to the native patella. FIG. 6F illustrates a cross-section of patellar component 500 implanted onto prepared native patella 600. It should be understood that patellar component 500 may include a transitional zone 540 between the body 520 and the articular surface 530. For example, if body 520 is formed of a porous titanium and articular surface 530 is formed of PAEK/PEEK or a polyethylene material, transitional zone 540 may include both materials in a gradient, with the transition zone including more metal nearer body 520 and more PAEK/PEEK or polyethylene (or other suitable polymer) nearer articular surface 530.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A prosthetic knee implant system comprising:
   a prosthetic femoral component having a lateral condyle, a medial condyle, a bone-contacting surface, and an articular surface;
   a tibial component including:
      a base with a lateral condylar portion having a lateral recess formed therein and a medial condylar portion having a medial recess formed therein, the base having a bone-contacting surface and a second surface opposite the bone-contacting surface, the medial and lateral recesses extending a depth into the second surface;
      a lateral bearing insert secured within the lateral recess in an assembled condition of the tibial component, the lateral bearing insert having a flat proximal surface for articulation with the lateral condyle of the femoral component;
      a medial bearing insert secured within the medial recess in the assembled condition of the tibial component, the medial bearing insert having a flat proximal surface for articulation with the medial condyle of the femoral component;
      a flexible lateral meniscal component positioned at least partially within the lateral recess and having a main contact surface extending around a circumference of the lateral insert and extending proximally of the second surface for supporting and directly contacting the lateral condyle of the femoral component in the assembled condition of the tibial component; and
      a flexible medial meniscal component positioned at least partially within the medial recess and having a main contact surface extending around a circumference of the medial insert and extending proximally of the second surface for supporting and directly contacting the medial condyle of the femoral component in the assembled condition of the tibial component;
   wherein the base includes a bridge coupling the lateral condylar portion to the medial condylar portion so that an anterior notch is formed between the medial and lateral condylar portions anterior to the bridge, and a posterior notch is formed between the medial and lateral condylar portions posterior to the bridge.

2. The system of claim 1, wherein the base includes a medial protrusion extending distally from the bone-contacting surface of the medial condylar portion and a lateral protrusion extending distally from the lateral condylar portion.

3. The system of claim 2, wherein the medial and lateral protrusions are each substantially "D"-shaped.

4. The system of claim 3, wherein the medial protrusion and lateral protrusion each include a distal surface formed of porous metal.

5. The system of claim 1, wherein the bone-contacting surfaces of the femoral component and the tibial component are each at least partially formed of porous metal, the medial and lateral inserts are each at least partially formed of polyethylene, the articular surface of the femoral component is at least partially formed of a polyaryl ether ketone ("PAEK"), and the medial and lateral meniscal components are each at least partially formed of polyurethane.

6. The system of claim 1, wherein the second surface is formed of polished metal.

7. The system of claim 1, wherein the second surface is coated with PAEK.

8. The system of claim 1, wherein the medial meniscal component includes a side wall and a peripheral rim extending radially outward of the side wall, and the lateral meniscal component includes a side wall and a peripheral rim extending radially outward of the side wall, and in the assembled condition of the tibial component the second surface of the base overlies the peripheral rims of the medial and lateral meniscal components.

9. The system of claim 1, wherein the bone-contacting surface of the femoral component includes a main contact surface and a peripheral rim extending along a perimeter of the main contact surface of the femoral component, the peripheral rim of the femoral component extending substantially orthogonally away from the main contact surface of the femoral component.

10. The system of claim 1, wherein the main contact surfaces of the medial and lateral meniscal components are wedge-shaped such that portions of the medial and lateral components nearer the bridge extend a greater height proximal to the second surface than portions of the medial and lateral components positioned farther away from the bridge in the assembled condition of the tibial component.

11. A prosthetic knee implant system comprising:
   a prosthetic femoral component having a lateral condyle, a medial condyle, a bone-contacting surface, and an articular surface;
   a tibial component including:
      a base with a lateral condylar portion having a lateral recess formed therein and a medial condylar portion having a medial recess formed therein, the base having a bone-contacting surface and a second surface opposite the bone-contacting surface, the medial and lateral recesses extending a depth into the second surface;
      a lateral bearing insert secured within the lateral recess in an assembled condition of the tibial component, the lateral bearing insert having a flat proximal surface for articulation with the lateral condyle of the femoral component;
      a medial bearing insert secured within the medial recess in the assembled condition of the tibial component, the medial bearing insert having a flat proximal surface for articulation with the medial condyle of the femoral component;
      a flexible lateral meniscal component positioned at least partially within the lateral recess and having a main contact surface extending around a circumference of the lateral insert and extending proximally of the second surface for supporting the lateral condyle of the femoral component in the assembled condition of the tibial component; and
      a flexible medial meniscal component positioned at least partially within the medial recess and having a main contact surface extending around a circumference of the medial insert and extending proximally of the second surface for supporting the medial condyle of the femoral component in the assembled condition of the tibial component;
   wherein the base includes a bridge coupling the lateral condylar portion to the medial condylar portion so that an anterior notch is formed between the medial and lateral condylar portions anterior to the bridge, and a posterior notch is formed between the medial and lateral condylar portions posterior to the bridge; and
   wherein the medial meniscal component includes a side wall and a peripheral rim extending radially outward of the side wall, and the lateral meniscal component includes a side wall and a peripheral rim extending radially outward of the side wall, and in the assembled condition of the tibial component the second surface of the base overlies the peripheral rims of the medial and lateral meniscal components.

12. The system of claim 11, wherein the base includes a medial protrusion extending distally from the bone-contacting surface of the medial condylar portion and a lateral protrusion extending distally from the lateral condylar portion.

13. The system of claim 12, wherein the medial and lateral protrusions are each substantially "D"-shaped.

14. The system of claim 13, wherein the medial protrusion and lateral protrusion each include a distal surface formed of porous metal.

15. The system of claim 11, wherein the bone-contacting surfaces of the femoral component and the tibial component are each at least partially formed of porous metal, the medial and lateral inserts are each at least partially formed of polyethylene, the articular surface of the femoral component is at least partially formed of a polyaryl ether ketone ("PAEK"), and the medial and lateral meniscal components are each at least partially formed of polyurethane.

16. The system of claim 11, wherein the second surface is formed of polished metal.

17. The system of claim 11, wherein the second surface is coated with PAEK.

18. The system of claim 11, wherein the bone-contacting surface of the femoral component includes a main contact surface and a peripheral rim extending along a perimeter of the main contact surface of the femoral component, the peripheral rim of the femoral component extending substantially orthogonally away from the main contact surface of the femoral component.

19. The system of claim 11, wherein the main contact surfaces of the medial and lateral meniscal components are wedge-shaped such that portions of the medial and lateral components nearer the bridge extend a greater height proximal to the second surface than portions of the medial and lateral components positioned farther away from the bridge in the assembled condition of the tibial component.

* * * * *